(12) United States Patent
D'Albini et al.

(10) Patent No.: US 12,073,931 B2
(45) Date of Patent: Aug. 27, 2024

(54) ALTERNATE DOSE REGIMEN IDENTIFICATION SYSTEM

(71) Applicant: Express Scripts Strategic Development, Inc., St. Louis, MO (US)

(72) Inventors: Lesley A. D'Albini, Spring Hill, KS (US); William J. Wright, Marion, AR (US); Sid Phadke, Memphis, TN (US); Mark Jacob, St. Louis, MO (US); Mary M. Dorholt, Maple Grove, MN (US)

(73) Assignee: Express Scripts Strategic Development, Inc., St. Louis, MO (US)

( * ) Notice: Subject to any disclaimer, the term of this patent is extended or adjusted under 35 U.S.C. 154(b) by 248 days.

(21) Appl. No.: 17/841,320

(22) Filed: Jun. 15, 2022

(65) Prior Publication Data
US 2023/0410968 A1     Dec. 21, 2023

(51) Int. Cl.
*G16H 20/10*     (2018.01)
*G16H 40/20*     (2018.01)

(52) U.S. Cl.
CPC ............. *G16H 20/10* (2018.01); *G16H 40/20* (2018.01)

(58) Field of Classification Search
CPC ................................ G16H 40/02; G16H 20/10
See application file for complete search history.

(56) References Cited

U.S. PATENT DOCUMENTS

| | | | |
|---|---|---|---|
| 8,382,696 B2 * | 2/2013 | Beiriger ................. | G16H 20/40 604/6.11 |
| 8,676,608 B2 * | 3/2014 | Oesterheld ............. | G06Q 50/22 705/3 |
| 9,132,061 B2 * | 9/2015 | Beiriger ................. | A61M 5/162 |
| 9,138,379 B2 * | 9/2015 | Beiriger ................. | A61M 5/36 |
| 9,283,145 B2 * | 3/2016 | Beiriger ................. | A61M 5/142 |
| 9,852,267 B2 * | 12/2017 | Gaweda ................. | A61B 34/10 |
| 10,259,795 B2 * | 4/2019 | Page ....................... | C07D 277/06 |
| 10,387,406 B2 * | 8/2019 | Shiloh .................... | G06F 16/24 |
| 10,387,617 B2 * | 8/2019 | Bagwell ................. | G16H 70/40 |

(Continued)

OTHER PUBLICATIONS

Galen, 2014, pp. 1-6.*
Bekker, Cet al. "Pharmacists' activities to reduce medication waste: an international survey." Pharmacy 6.3 (2018): 94.

*Primary Examiner* — Michael I Ezewoko
(74) *Attorney, Agent, or Firm* — Schwegman Lundberg & Woessner, P.A.

(57) ABSTRACT

Methods and systems for performing dose regimen modification are provided. The methods and systems perform operations comprising: receiving prescription related data for treating a patient with an expected level of efficacy, the prescription related data comprising medication regimen information including dose and interval; determining, using a model, a first amount of drug waste based on the prescription related data; comparing the first amount of drug waste to a threshold value; and in response to determining that the first amount of drug waste transgresses the threshold value, identifying an alternate medication regimen that is associated with a treatment having a given level of efficacy corresponding to the expected level of efficacy, the alternate medication regimen being associated with a second amount of drug waste that is lower than the first amount of drug waste; and triggering a notification associated with the alternate medication regimen.

17 Claims, 9 Drawing Sheets

(56) References Cited

U.S. PATENT DOCUMENTS

| | | | | |
|---|---|---|---|---|
| 10,494,157 B2* | 12/2019 | Chang | | B65D 1/08 |
| 10,507,219 B2* | 12/2019 | Gilbert | | B65D 25/205 |
| 10,566,085 B2* | 2/2020 | Hanina | | G06V 20/48 |
| 10,692,590 B2* | 6/2020 | Wei | | G16H 10/20 |
| 10,930,380 B2* | 2/2021 | Pulitzer | | G16H 40/67 |
| 11,467,170 B2* | 10/2022 | Shinzato | | G01N 33/726 |
| 11,521,728 B2* | 12/2022 | Bagwell | | A61J 1/03 |
| 2001/0001144 A1* | 5/2001 | Kapp | | G16H 20/10 |
| | | | | 604/131 |
| 2006/0252830 A1* | 11/2006 | Brandon | | A61K 45/06 |
| | | | | 514/557 |
| 2006/0252831 A1* | 11/2006 | Offen | | A61K 33/06 |
| | | | | 514/557 |
| 2013/0085772 A1* | 4/2013 | Gaweda | | G16Z 99/00 |
| | | | | 705/2 |
| 2013/0317839 A1* | 11/2013 | Creswell | | G16H 10/60 |
| | | | | 705/2 |
| 2014/0052465 A1* | 2/2014 | Madan | | G16Z 99/00 |
| | | | | 705/2 |
| 2014/0100829 A1* | 4/2014 | Mould | | G16H 20/10 |
| | | | | 703/2 |
| 2014/0156064 A1* | 6/2014 | Crawford | | G16H 20/10 |
| | | | | 700/236 |
| 2017/0177812 A1* | 6/2017 | Sjölund | | G16H 20/40 |
| 2017/0372018 A1* | 12/2017 | Rosenblatt | | G16H 50/20 |
| 2018/0060517 A1* | 3/2018 | Bagwell | | G16H 20/60 |
| 2018/0101640 A1* | 4/2018 | Gaweda | | A61B 34/10 |
| 2018/0218782 A1* | 8/2018 | Spotts | | G16H 50/50 |
| 2019/0144174 A1* | 5/2019 | Chang | | B65D 1/08 |
| | | | | 604/295 |
| 2019/0194151 A1* | 6/2019 | Page | | C07D 277/06 |
| 2019/0258169 A1* | 8/2019 | Wang | | G03F 7/70558 |
| 2019/0287013 A1* | 9/2019 | Li | | G16H 50/20 |
| 2019/0355459 A1* | 11/2019 | Li | | G16H 50/20 |
| 2020/0200770 A1* | 6/2020 | Shinzato | | G01N 33/726 |
| 2020/0223598 A1* | 7/2020 | Chang | | B65D 47/18 |
| 2020/0411153 A1* | 12/2020 | Bagwell | | A61J 7/0418 |
| 2021/0012872 A1* | 1/2021 | Gaweda | | G16Z 99/00 |
| 2021/0082583 A1* | 3/2021 | Ehrlich | | H04W 4/023 |
| 2022/0076799 A1* | 3/2022 | Engelhardt | | G16H 50/20 |
| 2022/0157435 A1* | 5/2022 | Wu | | G16H 20/70 |
| 2022/0184311 A1* | 6/2022 | Goldsmith | | G16H 40/63 |
| 2022/0367025 A1* | 11/2022 | Cooper, IV | | G16H 10/60 |
| 2023/0145898 A1* | 5/2023 | Davies | | G16H 20/10 |
| | | | | 705/2 |
| 2023/0223125 A1* | 7/2023 | Gaweda | | G06N 3/08 |
| | | | | 705/2 |

* cited by examiner

ALTERNATE DOSE REGIMEN IDENTIFICATION SYSTEM

BACKGROUND

Certain patients are placed on medication regimens with certain drug dose and delivery intervals. Such prescribed dose and delivery intervals can be fulfilled by delivering the drugs through vials having predetermined drug quantities. The combination of vials used to deliver the prescribed dose and interval can result in drug waste by delivering more of the drug than is actually needed or prescribed.

DETAILED DESCRIPTION

Figure 1:
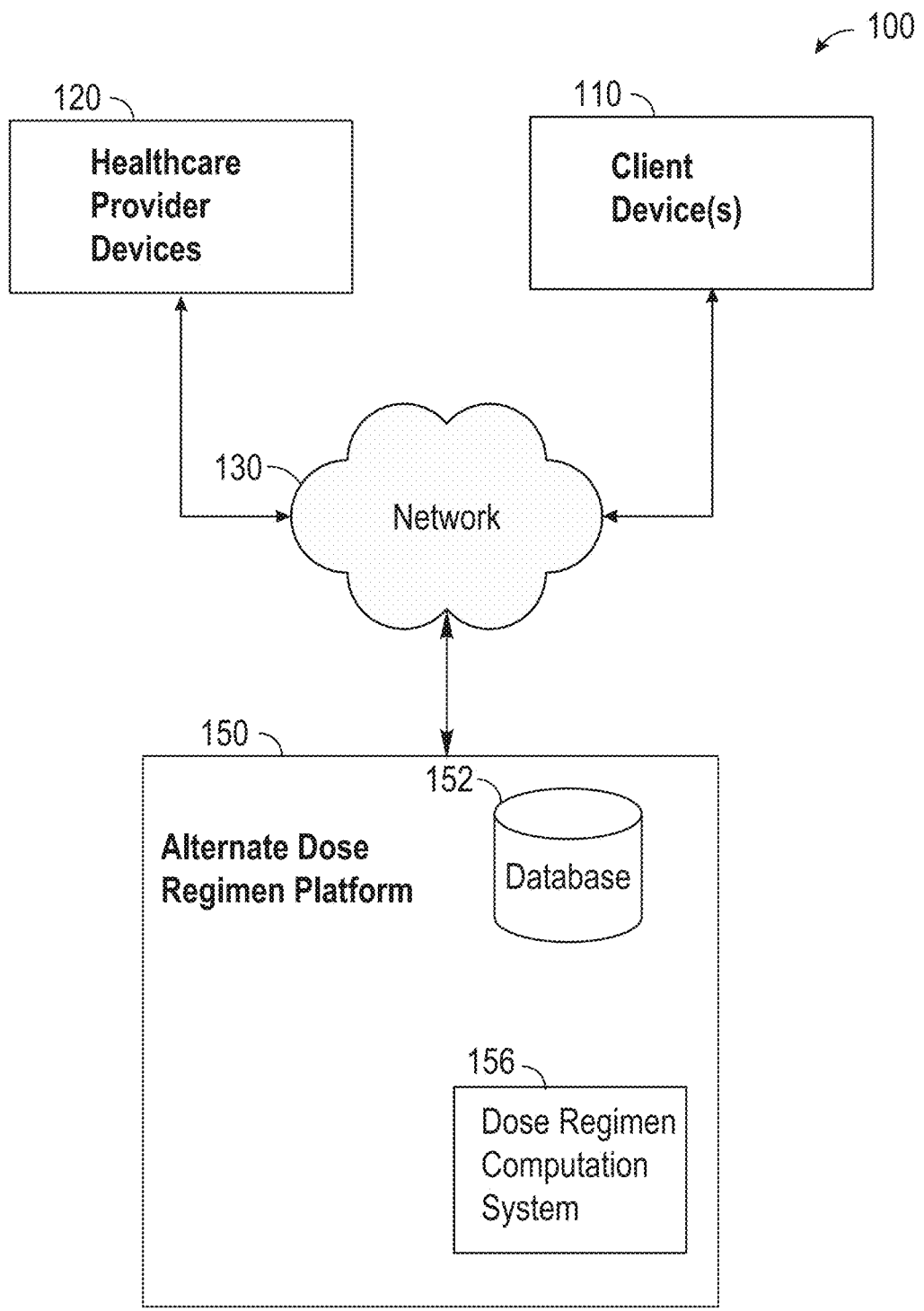
FIG. 1 is a block diagram of an example alternate dose regimen platform, according to some embodiments.

Example methods and systems for a medication dispensing system are provided. Specifically, the methods and systems provide recommendations for alternate dose regimens to satisfy a given prescription. In the following description, for purposes of explanation, numerous specific details are set forth in order to provide a thorough understanding of example embodiments. It will be evident, however, to one of ordinary skill in the art that embodiments of the invention may be practiced without these specific details.

Some types of disease are treated through prescription of drugs that are delivered subcutaneously (SQ) over a specified interval (e.g., every day, every seven days, every 14 days, once per month, and so forth). The dose of the drug that is administered and the interval at which it is given can be determined based on patient weight and other factors. Certain drugs are prepackaged by the manufacturer into different single-use size vials (e.g., 30 mg/mL, 60 mg/0.4 mL, 105 mg/0.7 mL, and 150 mg/mL) some of which can be mixed together in a single syringe while others cannot. When a drug is packaged in a single-use vial, the overage in the vial cannot be stored and used with the next dose. This remainder in a vial after a dose can be overage and is not administered to a patient. In order to achieve a certain prescribed dose, a pharmacist or doctor selects a particular combination of vials. For example, to achieve a 240 mg dose over a 14 day interval, one combination of vials that can be selected would include one drug vial having a 105 mg size and another 150 mg dose vial. This particular combination can result in dispensing over the prescribed dose and waste amount of the drug in the amount of 15 mg (e.g., 240 mg dose needed minus 255 mg drug dispensed). In addition to drug wasting, money is also wasted paying for the additional 15 mg of the drug which is discarded. Prescribers and pharmacists usually do not attempt to find the best combination of the drug vials to dispense to reduce drug waste and cost. In order to find the most economical solution that results in the least amount of drug waste, the present disclosure describes embodiments to compute at least one dose associated with a multitude of drug vial combinations and also consider by how much a dispensed dose can be reduced or increased to achieve a same level of efficacy as a prescribed dose. The process may also consider in the optimal drug vial combination to account for side effects and other criteria which can end up harming the patient.

The disclosed embodiments provide systems and methods to reduce drug waste, reduce cost and improve the overall process for dispensing drugs. Specifically, the disclosed embodiments implement a model that is applied to a given prescribed dose and interval and identifies and/or recommends an alternate dose regimen that achieves the same or similar (within a threshold amount) level of efficacy. The model may be a predictive model or other machine implemented model. In some examples, the model generates an output that is presented on an interactive graphical user interface of a machine. The graphical user interface can present a prescribed dose regimen and provides visual identifiers of a plurality (e.g., more or less than twenty, thirty, forty or the like) different alternate dose regimens that achieve the same level of treatment efficacy. Each of the different dose regimens can be associated with a respective drug dose vial combination and/or delivery interval to achieve a given prescribed dose. Input can be received that interacts and selects between the different visual identifiers. In response to such an input, a notification, alert or message can be presented that identifies the specific combination of drug dose vials, interval and level of drug waste (and/or cost). In some examples, the model implements a trained machine learning technique or model (e.g., a neural network) that can predict a given alternate dose regimen given a prescribed dose regimen. The output of the machine learning model can be used to visually identify one or more of the visual identifiers to recommend for selection. This further improves the overall process of drug dispensing and fulfillment.

Pharmacies can use the disclosed system to provide fulfillment counseling to patients and/or doctors and provide the rationale for the method in which each of their medications will be dispensed and optimize downstream fulfillment workflow. According to some embodiments, prescription related data for treating a patient with an expected level of efficacy is received. The prescription related data can include medication regimen information including dose and interval. A model is applied to the prescription related data to determine an amount of drug waste. In response to determining that the amount of drug waste transgresses a threshold value, an alternate medication regimen is identified that is associated with treatment having a given level of efficacy corresponding to the expected level of efficacy of the prescription related data. The alternate medication regimen can be associated with a lower amount of drug waste than the amount of drug waste associated with the dose and interval of the medication regiment. According to the disclosed techniques, a notification is triggered associated with the identified alternate medication regimen.

In this way, the disclosed embodiments improve the overall process of medication fulfillment and specifically improves the efficiency at which drug vial combinations are selected for fulfilling a given prescription while reducing cost and waste associated with the drugs.

FIG. 1 is a block diagram showing an example alternate dose regimen system 100 according to various exemplary embodiments. The alternate dose regimen system 100 includes one or more client devices 110, one or more healthcare provider devices 120, and an alternate dose regimen platform 150 that are communicatively coupled over a network 130 (e.g., Internet, telephony network).

As used herein, the term "client device" may refer to any machine that interfaces to a communications network (such as network 130) to access the alternate dose regimen platform 150. The client device 110 may be, but is not limited to, a mobile phone, desktop computer, laptop, portable digital assistants (PDAs), smart phones, a wearable device (e.g., a smart watch), tablets, ultrabooks, netbooks, laptops, multi-processor systems, microprocessor-based or programmable consumer electronics, game consoles, set-top boxes, or any other communication device that a user may use to access a network or the alternate dose regimen platform 150.

In some cases, the alternate dose regimen platform 150 is accessible over a global communication system, e.g., the Internet or world wide web, or a limited communication network such as an intranet. In such instances, the alternate dose regimen platform 150 hosts a website that is accessible to the client devices 110. Upon accessing the website, the client devices 110 provide secure login credentials, which are used to access a profile associated with the login credentials. One or more user interfaces associated with the alternate dose regimen platform 150 are provided over the Internet via the website to the client devices 110.

Healthcare provider devices 120 can include the same or similar functionality as client devices 110 for accessing the alternate dose regimen platform 150. In some cases, the healthcare provider devices 120 are used by "internal" users. Internal users are personnel, such as physicians, clinicians, healthcare providers, health-related coaches pharmacy benefit manager (PBM) operators, pharmacists, specialty pharmacy operators or pharmacists, or the like that are associated with or employed by an organization that provides the alternate dose regimen platform 150. In some cases, the healthcare provider devices 120 are used by "external" users. External users are personnel, such as physicians, clinicians, and health-related coaches that are associated with or employed by a different (external) organization than that which provides the alternate dose regimen platform 150.

The healthcare provider devices 120, when used by internal or external users, to access the alternate dose regimen platform 150 can view many records associated with many different patients (or users associated with client devices 110). Different levels of authorization can be associated with different internal and different external users to control which records the internal and external users have access. In some instances, only records associated with those patients to which a given internal or external user is referred, are made accessible and available to the given internal or external user device. Sometimes, a first internal or external user can refer a patient or records associated with the patient to a second internal or external user. In such circumstances, the second internal or external user becomes automatically authorized to access and view the patient's records that were referred by the first internal or external user. In an example embodiment, an outreach event or flag can be set in a patient record in the database at the alternate dose regimen platform 150 in response to the dose regimen computation system 156 determining that an amount of drug waste associated with one or more medication regimens or prescriptions specifying dose and delivery interval associated with a given patient transgress (exceed or fall below) a threshold value (e.g., 14 mg per dose). The referral event or flag provides authorization to a user of the healthcare provider devices 120 to view patient records and contact the patient or physician (e.g., to discuss alternate medication regimen).

The alternate dose regimen platform 150 can be applied to any prescription related to a drug that includes monoclonal or bi-specific antibodies with linear, $1^{st}$ order pharmacokinetics, following any required loading doses necessary to establish baseline steady-state plasma concentrations. For example, the alternate dose regimen platform 150 can be applied to emicizumab which is a recombinant, humanized, bispecific antibody (IgG4) capable of binding FIXa and FX, restoring the intrinsic cascade by providing a bridge over the missing FVIII, rendering its absence obsolete. Namely, the emicizumab can be used to treat patients with hemophilia A. In some examples, emicizumab or other disclosed drug can be made available in four strengths: 30 mg per mL, 60 mg per 0.4 mL, 105 mg per 0.7 mL, and 150 mg per mL, all as single-use vials. Vials with the same concentration can be combined in the same syringe to decrease injection burden. In some examples, once a single dose reaches 90 mg, the amount of drug wasted may not exceed 14 mg. According to the disclosed techniques, at this dose threshold, any wastage greater than 14 mg can be reduced or eliminated by using an alternate vial combination, as discussed below, such as by triggering the referral event or flag. In some examples, the drug manufacturer provides a guide including vial combination options for doses from 9-900 mg per dose which can be used to recommend or identify one or more alternate dose regimens. However, the present methods and systems can be applied to drugs other monoclonal drugs or bi-specific antibodies containing drugs.

In some examples, the referral event or flag causes a graphical user interface to be generated that represents the prescribed dose and interval and associated drug waste in a prescription region. The graphical user interface can include a plurality of interactive regions representing different medication regimens. The graphical user interface can include a first plurality indicators representing a first set of alternate medication regimens having a first level of accuracy. The graphical user interface can include a second plurality indicators representing a first set of alternate medication regimens having a second level of accuracy. The graphical user interface can receive input that selects a given indicator of the first plurality of indicators or the second plurality of indicators. In response, the graphical user interface can update the prescription region to represent a drug dose vial combination and interval associated with a given alternate medication regimen represented by the given indicator and to represent drug waste associated with the given alternate medication regimen.

In some examples, the graphical user interface can also include a third plurality of indicators that represent medication regimens of the first and second sets of alternate medication regimens having a specified type of drug dose vial (e.g., a 30 mg drug dose vial). In some examples, the specified type of drug dose vial can correspond to a drug dose vial that cannot be combined in a syringe with other drug dose vials (e.g., because an unstudied concentration can result). In some examples, the specified type of drug dose vial can correspond to a drug dose vial that is associated with a low or high level of adherence, efficacy, and/or side effects.

In some examples, the alternate dose regimen platform 150 can implement a machine learning technique, such as a neural network (discussed below in connection with FIG. 9). The machine learning technique can be trained to establish a relationship between a plurality of training prescription related data features and alternate medication regimens. In an example, the machine learning technique can be trained by obtaining a batch of training data comprising a first set of the plurality of training prescription related data features and alternate medication regimens that have been selected. The first set of the plurality of training prescription related data features is processed by the machine learning technique to generate an estimated alternate medication regimen. A loss can be computed based on a deviation between the estimated alternate medication regimen and the corresponding alternate medication regimens of the first set of the plurality of training prescription related data features. Parameters of the machine learning technique can then be updated based on the computed loss. These training operations can be repeated for multiple batches of training data and/or until a stopping criterion is reached.

The network 130 may include, or operate in conjunction with, an ad hoc network, an intranet, an extranet, a virtual private network (VPN), a local area network (LAN), a wireless network, a low energy Bluetooth (BLE) connection, a WiFi direct connection, a wireless LAN (WLAN), a wide area network (WAN), a wireless WAN (WWAN), a metropolitan area network (MAN), the Internet, a portion of the Internet, a portion of the Public Switched Telephone Network (PSTN), a plain old telephone service (POTS) network, a cellular telephone network, a wireless network, a Wi-Fi® network, another type of network, or a combination of two or more such networks. For example, a network or a portion of a network may include a wireless or cellular network and the coupling may be a Code Division Multiple Access (CDMA) connection, a Global System for Mobile communications (GSM) connection, or other type of cellular or wireless coupling. In this example, the coupling may implement any of a variety of types of data transfer technology, such as Single Carrier Radio Transmission Technology (1×RTT), Evolution-Data Optimized (EVDO) technology, General Packet Radio Service (GPRS) technology, Enhanced Data rates for GSM Evolution (EDGE) technology, third Generation Partnership Project (3GPP) including 3G, fourth generation wireless (4G) networks, fifth generation wireless (5G) networks, Universal Mobile Telecommunications System (UMTS), High Speed Packet Access (HSPA), Worldwide Interoperability for Microwave Access (WiMAX), Long Term Evolution (LTE) standard, others defined by various standard setting organizations, other long range protocols, or other data transfer technology.

The healthcare provider devices 120 can be used to access pharmacy claims, medical data (e.g., medical information 230 stored in database 152), laboratory data and the like for one or more patients that the healthcare provider devices 120 are authorized to view. This patient information 210 can be maintained in a database 152 by the alternate dose regimen platform 150 or in a third-party database accessible to the alternate dose regimen platform 150 and/or the healthcare provider devices 120.

In some embodiments, the client devices 110 and the alternate dose regimen platform 150 can be communicatively coupled via an audio call (e.g., VoIP, Public Switched Telephone Network, cellular communication network, etc.) or via electronic messages (e.g., online chat, instant messaging, text messaging, email, and the like). While FIG. 1 illustrates a single client device 110 and a single healthcare provider device 120, it is understood that a plurality of such devices can be included in the system 100 in other embodiments. As used herein, the term "client device" may refer to any machine that interfaces to a communications network (such as network 130) to obtain resources from one or more server systems or other client devices.

The alternate dose regimen platform 150 can be a human agent or an automated agent, e.g., on behalf of an organization. The automated agent can be associated with a medical group that includes the member. The automated agent can be an interactive voice response (IVR), a virtual online assistant, or a chatbot provided on a website. During a communication session between the user and the agent, the alternate dose regimen platform 150 identifies the member using initial context data (e.g., the phone number the member is calling from, the website login information inputted, automatic number identification (ANI), etc.) and retrieves the data on the member (e.g., member account information, name, address, insurance information, information on spouse and dependents, etc.) to be presented on the client device 110.

In some embodiments, the alternate dose regimen platform 150 includes a dose regimen computation system 156. As explained in more detail in connection with FIG. 3, the dose regimen computation system 156 is trained based on training prescription related data features and their corresponding ground-truth alternate medication regimens. The dose regimen computation system 156 is trained to predict an alternate medication regimen (e.g., particular set of drug vials and interval) for each medication regimen (e.g., a given set of drug vials and interval) associated with a given patient prescription. The prediction can be used to generate an alert or provide an indicator or notification to a prescriber or pharmacist to select an alternate medication regimen to reduce drug waste and cost (and, in some cases to reduce side effects, bleeding and/or patient burden in taking a given medication).

Figure 2:
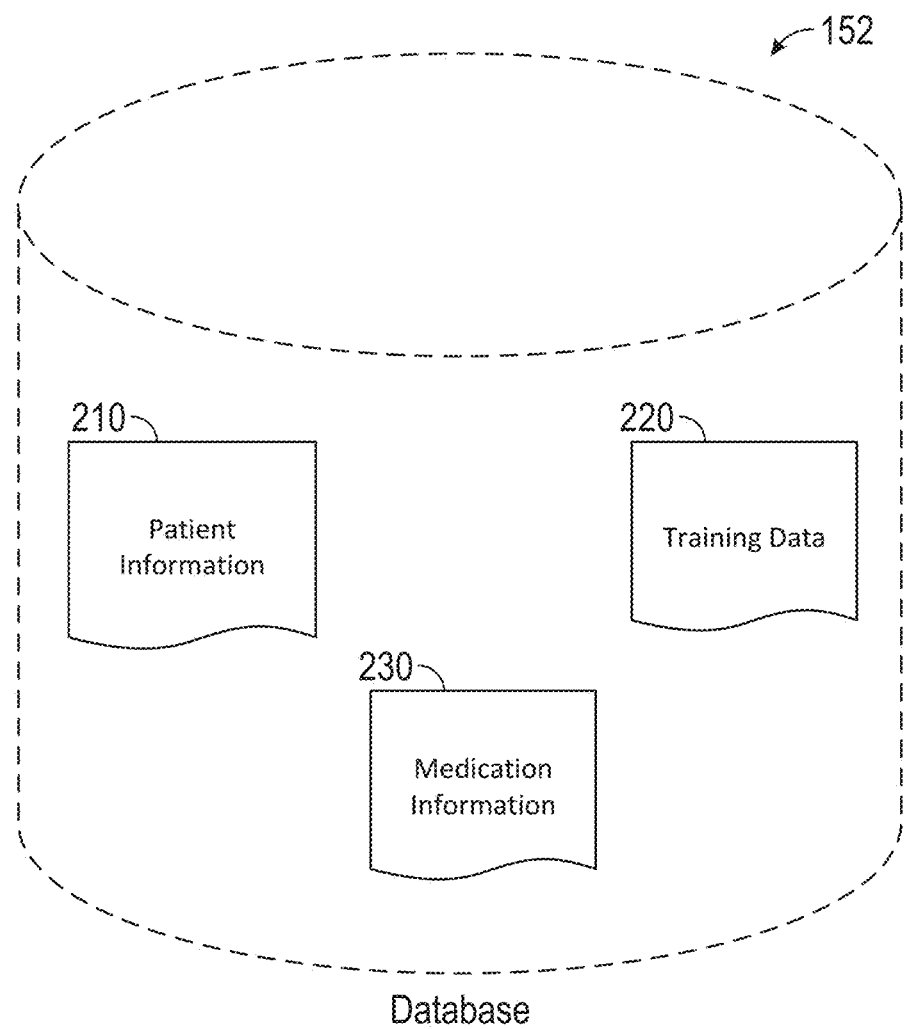
FIG. 2 is an example database that may be deployed within the system of FIG. 1, according to some embodiments.

FIG. 2 is an example database 152 that may be deployed within the system of FIG. 1, according to some embodiments. The database 152 includes patient information 210, medication information 230, and training data 220. The patient information 210 can be generated by the alternate dose regimen platform 150. For example, the alternate dose regimen platform 150 can access one or more patient records from one or more sources, including pharmacy claims, benefit information, prescribing physician information, dispensing information (e.g., where and how the patient obtains their current medications), demographic information, prescription information including dose and interval, and so forth. The alternate dose regimen platform 150 can collect this information from the patient records and generates a patient features vector that includes this information and/or a prescription features vector.

The medication information 230 stores various medication related information (e.g., prescriptions, size of the medication or pills, compatible forms of dispensing information, temperature control information, mixing exclusion information, and so forth) for various medications. The size of the medication or pills may be used to determine whether such medication can be dispensed using an alternate dispensing method. The compatible forms of dispensing information can indicate or list the way in which the medication can be dispensed, such as through typical pill bottle, multiple-dose packages, specialty pharmacy, home delivery, and so forth. The medication information 230 can also include a list of different vial sizes and measures that are associated with a particular medication and their associated doses and intervals. The medication information 230 can also store information for each medication indication which vials can be mixed together into a single syringe and which cannot. Such medication information 230 is used by the alternate dose regimen platform 150 to identify and recommend an alternate dose regimen given a particular prescribed dose regime.

The training data 220 includes training prescription related data features and alternate medication regimens that have been selected. The training data 220 is used to train a machine learning model implemented by the dose regimen computation system 156 to generate estimates of one or more alternate medication regimens. For example, the training data 220 can be built over time by identifying a set of prescriptions for particular medications which were successfully converted to an alternate medication regimen. The training data 220 can also store information about which alternate medication regimens are associated with levels of adherence that exceed a threshold value and which are associated with levels of adherence below the threshold value. The training data 220 can also store preference information for various categories or groups of individuals, such as by age group, indicating the types of medication regimens which are preferred (e.g., single dose or single injection with a particular dose versus multiple injections to make up the particular dose).

Once such patients are identified, the patients and/or physicians or doctors are contacted to convert from their current prescribed medication regimen to an alternate medication regimen. If the patients and/or physicians agree to the conversion, the training data 220 is updated to indicate a successful conversion. If the patients and/or physicians do not agree to the conversion, the training data 220 is updated to indicate an unsuccessful conversion. After a specified quantity of patients and medications are processed, the features are generated and stored in the training data 220 and used to train the machine learning model of the regimen computation system 156.

Figure 3:
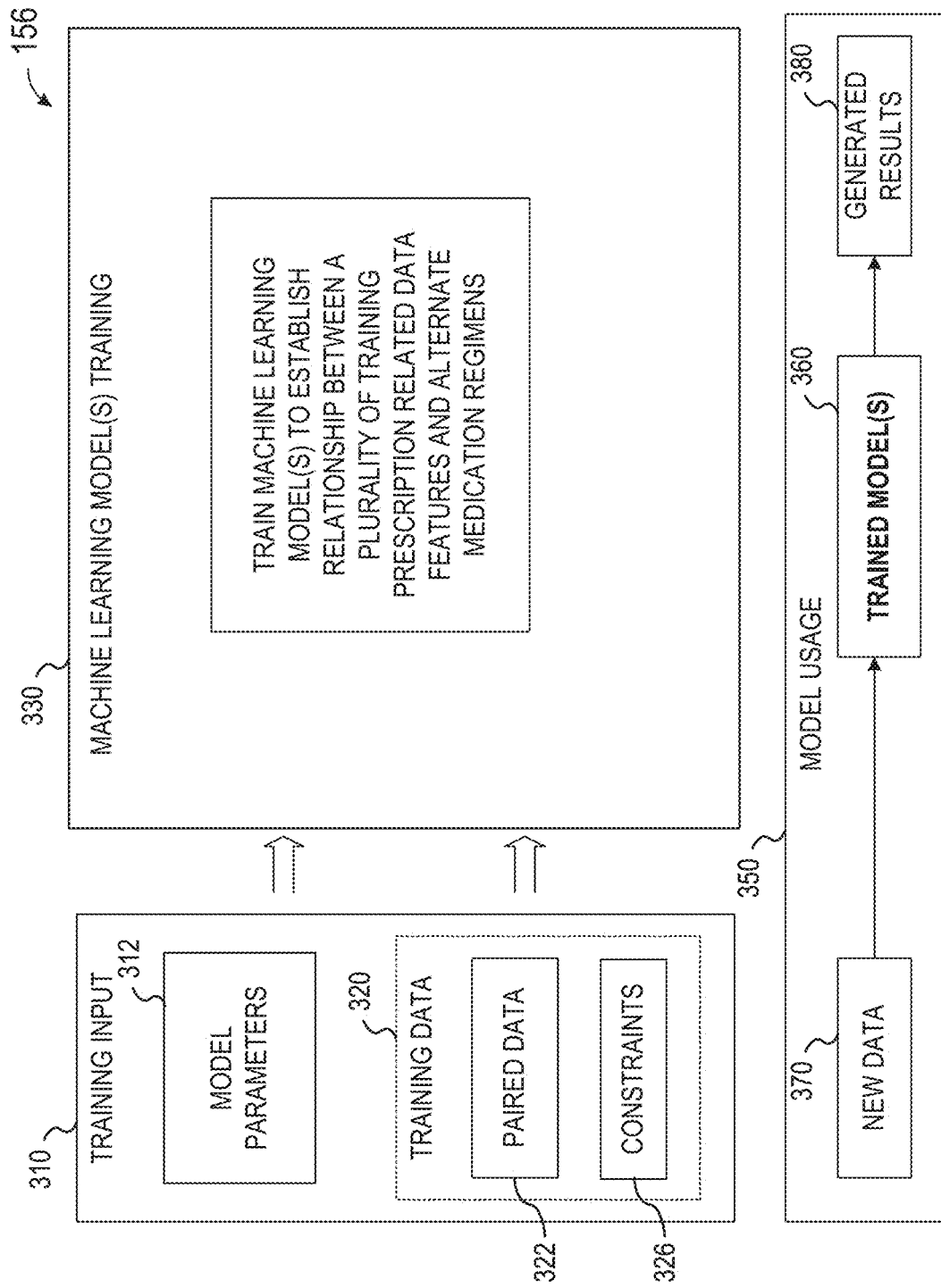
FIG. 3 is a block diagram of an example dose regimen computation system that may be deployed within the system of FIG. 1, according to some embodiments.

FIG. 3 is a block diagram of an example dose regimen computation system 156 that may be deployed within the system of FIG. 1, according to some embodiments. Training input 310 includes model parameters 312 and training data 320 (e.g., training data 220 (FIG. 2)) which may include paired training data sets 322 (e.g., input-output training pairs) and constraints 326. Model parameters 312 stores or provides the parameters or coefficients of corresponding ones of machine learning models. During training, these parameters 312 are adapted based on the input-output training pairs of the training data sets 322. After the parameters 312 are adapted (after training), the parameters are used by trained models 360 to implement the trained machine learning models on a new set of data 370.

Training data 320 includes constraints 326 which may define the constraints of a given medication or collection of medications, such as the types of medications and restrictions associated with such medications (e.g., whether or not the medication vials can be mixed together or stored together with other medications and temperature control restrictions for the medications). The paired training data sets 322 may include sets of input-output pairs, such as a pairs of a plurality of training prescription related data features and alternate medication regimens that have been selected. Some components of training input 310 may be stored separately at a different off-site facility or facilities than other components.

Machine learning model(s) training 330 trains one or more machine learning techniques based on the sets of input-output pairs of paired training data sets 322. For example, the model training 330 may train the machine learning (ML) model parameters 312 by minimizing a loss function based on one or more ground-truth alternate medication regimens. The ML model can include any one or combination of classifiers or neural networks, such as an artificial neural network, a convolutional neural network, an adversarial network, a generative adversarial network, a deep feed forward network, a radial basis network, a recurrent neural network, a long/short term memory network, a gated recurrent unit, an auto encoder, a variational autoencoder, a denoising autoencoder, a sparse autoencoder, a Markov chain, a Hopfield network, a Boltzmann machine, a restricted Boltzmann machine, a deep belief network, a deep convolutional network, a deconvolutional network, a deep convolutional inverse graphics network, a liquid state machine, an extreme learning machine, an echo state network, a deep residual network, a Kohonen network, a support vector machine, a neural Turing machine, and the like.

Particularly, the ML model can be applied to a training plurality of prescription related data features to estimate or generate a prediction of alternate medication regimens. In some implementations, a derivative of a loss function is computed based on a comparison of the estimated alternate medication regimens and the ground truth medication alternate medication regimens associated with the training prescription related data features and parameters of the ML model are updated based on the computed derivative of the loss function.

In one example, the ML model receives a batch of training data that includes a first set of the plurality of training prescription related data features together with alternate medication regimens that have been selected. For example, the ML model can receive a training prescription indicating a particular dose and interval for a given patient weight and the corresponding alternate medication regimen that was selected. Namely, the prescription can specify a first combination of vials to deliver a particular dose and the alternate medication regimen specify a different combination of vials to deliver the same or different dose and over the same or different interval. The ML model generates a feature vector based on the first set of the plurality of training prescription related data features and generates a prediction of one or more alternate medication regimens. The prediction is compared with the ground truth alternate medication regimens and parameters of the ML model are updated based on the comparison.

The result of minimizing the loss function for multiple sets of training data trains, adapts, or optimizes the model parameters 312 of the corresponding ML models. In this way, the ML model is trained to establish a relationship between a plurality of training prescription related data features and alternate medication regimens.

The ML model is trained in one implementation according to supervised learning techniques. In such cases, to train the ML model, a plurality of prescription related data features are retrieved together with their corresponding training alternate medication regimens. The ML model is applied to a first batch of training prescription related data features to estimate alternate medication regimens for each prescription in prescription related data features. The batch of the training prescription related data features can be used to train the ML model with the same parameters of the ML model and may range from one training prescription related data feature to all of the training prescription related data features. The estimated or predicted alternate medication regimens are compared with the ground-truth alternate medication regimens to compute a loss based on a loss function and a gradient or derivative of the loss function with the applied losses is computed. Based on the gradient or derivative of the loss function, updated parameters for the ML model are computed. The ML model is then applied with the updated parameters to a second batch of training data to again estimate a given set of alternate medication regimens which are applied to a loss function to compute loss based on the ground-truth alternate medication regimens. Parameters of the ML model are again updated and iterations of this training process continue for a specified number of iterations or epochs or until a given convergence criteria has been met.

After the machine learning model is trained, new data 370, including one or more prescription related data features are received (e.g., a particular dose and interval and corresponding combination of drug vials to achieve the dose and interval), may be received. The trained machine learning technique may be applied to the new data 370 to generate results 380 including a prediction of one or more alternate medication regimens.

The one or more alternate medication regimens are used to trigger a notification or generate a display of a graphical user interface to enable selection of an alternate medication regimen.

In some examples, prescription related data for treating a patient with an expected level of efficacy is received. The prescription related data can specify or include medication regimen information including dose and interval. For example, the prescription related data can specify a weight of the patient and a dose to be delivered to the patient. The prescription related data can be used to select a particular drug vial combination to deliver the dose. For example, if the dose to be delivered includes 190 mg of the drug over a 14 day period, a combination of drug vials can be specified by the prescription related data including two 105 mg vials. This can result in an overall dose of 210 mg being delivered which results in 20 mg of waste.

In some examples, a model is applied to the prescription related data to determine the amount of drug waste associated with the dose and interval. For example, the model can determine that a total of 20 mg of drug waste is associated with the received prescription. The output of the model including the total amount of drug waste can be compared to a threshold value. The threshold value can specify a maximum allowable drug waste and can specify a 14 mg (milligram) tolerance. In some examples, the dose regimen computation system 156 compares the determined drug waste of 20 mg to the threshold value. In response to determining that the drug waste transgresses the threshold value, the dose regimen computation system 156 can perform operations to select an alternate medication regimen. The alternate medication regimen can be associated with treatment having a given level of efficacy corresponding to the expected level of efficacy of the prescription related data. Namely, the alternate medication regimen can have the same overall level of efficacy as the prescribed dose and interval. The alternate medication regimen can be associated with a lower amount of drug waste than the amount of drug waste associated with the dose and interval of the medication regimen.

In some examples, as part of selecting an alternate medication regime, the dose regimen computation system 156 can generate a plurality of different medication regimens each being associated with the expected level of efficacy. Namely, the dose regimen computation system 156 can apply the patient weight and prescribed dose to a model to generate a set of different medication regimens that include different doses and/or that are delivered over the same or different interval than the prescribed dose. Each of the different medication regimens can be associated with a different combination of vials to achieve a given dose. In some examples, a first of the plurality of different medication regimens includes a second dose and the same interval as the prescribed medication regimen. The second dose can be greater than the first dose specified by the prescribed medication regimen. In some examples, a second of the plurality of different medication regimens includes a third dose and the same interval as the prescribed medication regimen. In some examples, the third dose is less than the first dose of the prescribed medication regimen. In some examples, a fourth of the plurality of different medication regimens includes a second dose and a second interval.

The dose regimen computation system 156 can obtain each of the different medication regimens and compute a drug waste for each medication regimen. For example, the dose regimen computation system 156 can add the dose of the vials specified by a given one of the different medication regimens and subtract that amount from a given dose to estimate the waste. The dose regimen computation system 156 then searches the waste associated with each of the different medication regimens to select a given medication regimen that satisfies a given criterion.

In some examples, the dose regimen computation system 156 selects as the given medication regimen the medication regimen that is associated with a least amount of waste or for which the waste value is below a specified threshold value (e.g., 14 mg per dose). In some examples, the dose regimen computation system 156 selects as the given medication regimen the medication regimen that is associated with zero waste.

In some examples, the criterion used to select the given medication regimen includes a combination of drug dose vials that is associated with a specified level of adherence, a specified level of side effects, injection quantity, or a specified level of efficacy. In such cases, the dose regimen computation system 156 can analyze or access information about each of the different medication regimens to determine a level of adherence, a specified level of side effects, injection quantity, or a specified level of efficacy of each different medication regimens. The dose regimen computation system 156 can select one of the given medication regimens for which the drug waste is below the drug waste computed for the prescribed medication regimen and for which the level of adherence, level of side effects, injection quantity, or level of efficacy corresponds to the specified level of adherence, specified level of side effects, injection quantity, or the specified level of efficacy, or at least one or at least two of these factors.

In some examples, the criterion used to select the given medication regimen includes an inventory parameter of the drug dose vials. In such cases, the dose regimen computation system 156 can access inventory information for each type (size) of drug vial associated with the prescribed medication. The inventory information can specify the total amount of vials available currently in stock. The inventor information can specify the rate at which certain types of drug vials (e.g., certain sizes of vials) are dispensed. Based on this information, the dose regimen computation system 156 can select a particular one of the different medication regimens that includes in the combination of vials used to deliver the drug a vial that is associated with a type of drug vial that is currently in stock, for which the amount of vials currently in stock exceed a stock threshold, and/or which is dispensed usually at a rate that exceeds a certain rate threshold.

The selection or selections made by the dose regimen computation system 156 can be represented in a graphical user interface that depicts each of the plurality of different medication regimens. The system 156 can compute the plurality of different medication regimens and develop a graphical representation that shows the prescribed regimen and all the therapeutically acceptable medication regimens that have a reduced waste profile relative to the prescribed regimen as further explained herein. The system 156 can be triggered when a threshold value of drug waste is exceeded or met.

Figure 4:
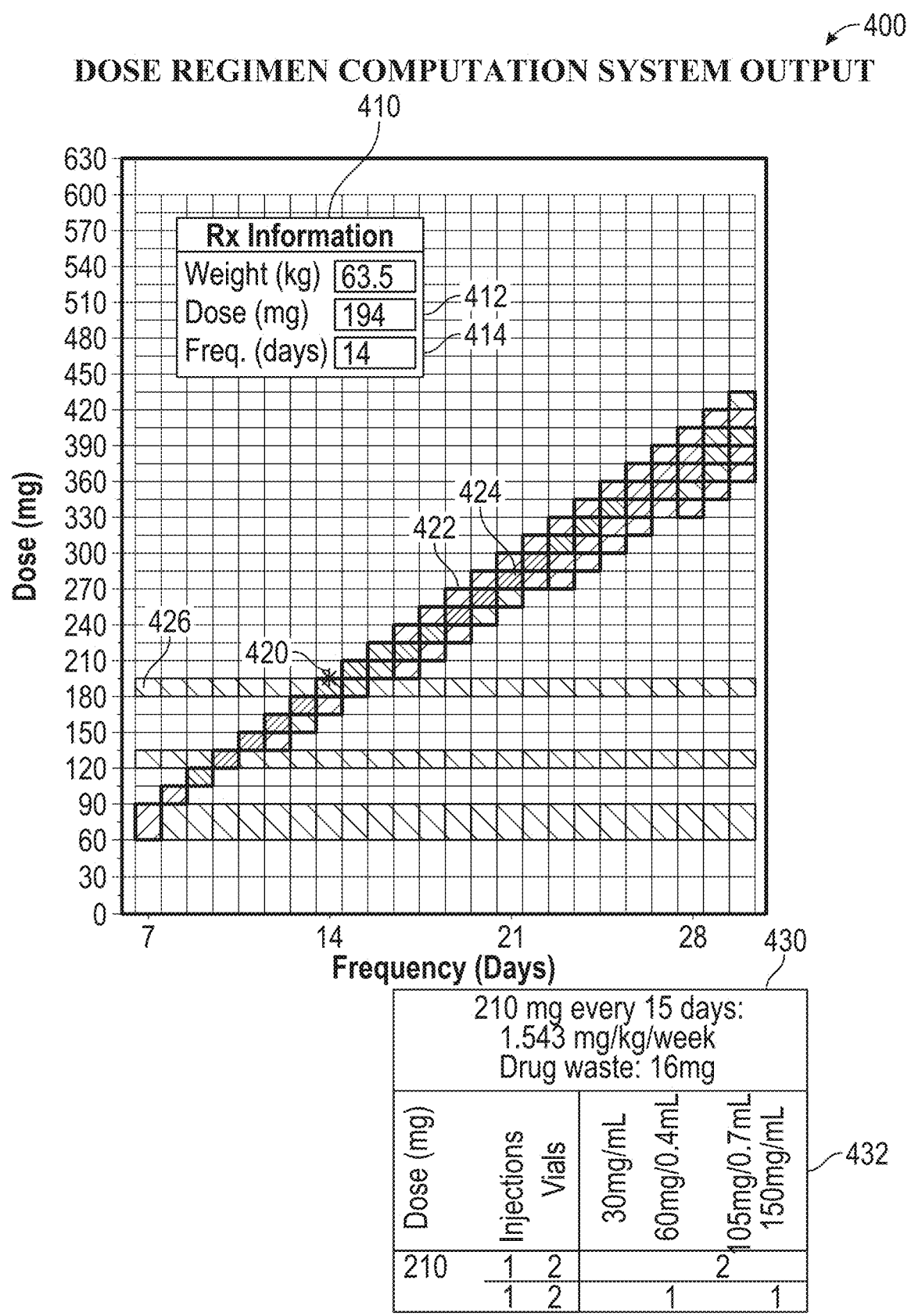
FIGS. 4 and 5 are example user interfaces of the alternate dose regimen platform, according to example embodiments.
Figure 5:
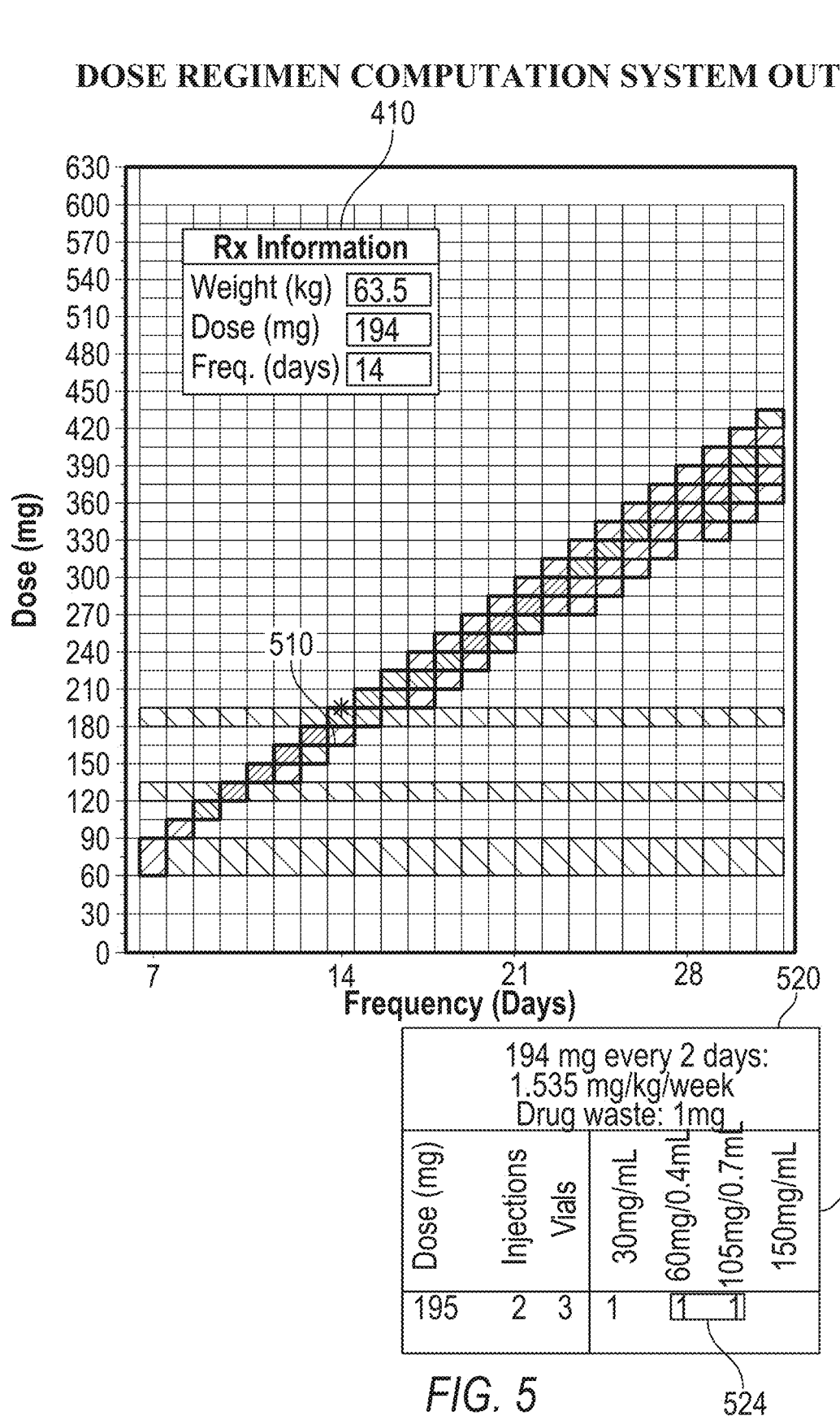

FIGS. 4 and 5 are example user interfaces 400 and 500 of the alternate dose regimen platform 156, according to example embodiments. The interactive graphical user interfaces 400 and 500 can represent an example notification that is triggered, such as in response to determines that the amount of drug waste transgresses the threshold value. In some examples, the alternate dose regimen platform 156 receives prescription information for a given patient that includes a prescribed dose regimen that specifies a dose or drug, an interval, and/or a combination of drug vials to dispense for the dose regimen.

In response to receiving the prescribed dose regimen, the alternate dose regimen platform 156 presents information received in the prescribed dose regimen in a prescription region or window 410. The prescription region or window 410 can be displayed as an overlay on top of a plot showing different alternate dose regimens. The alternate dose regimen platform 156 can present a weight of a patient, a dose (in milligrams) 412 and an interval (e.g., frequency in days) 414 in the prescription region or window 410. The alternate dose regimen platform 156 also identifies a corresponding point on the x-axis of the plot corresponding to the specified interval and the corresponding point on the y-axis corresponding to the prescribed dose. The alternate dose regimen platform 156 can present a first indicator 420 representing the prescribed dose regimen.

The alternate dose regimen platform 156 can access the amount of the drug contained in the drug vials corresponding to the first indicator 420 (associated with the prescribe dose). For example, the prescribed dose can include 194 mg of the drug every 14 days. The prescribed vials shown in the vial combination window 430 can include two 105 mg drug vials which total to 210 mg of drug. Based on the fact that the amount of drug contained in the prescribed vials exceeds the prescribed dose of 194 mg, the alternate dose regimen platform 156 can determine that the amount of drug waste is a waste value, in this example approximately 16 mg. The alternate dose regimen platform 156 can present an indicator in the vial combination window 430 that specifies the amount of drug waste that has been computed.

The alternate dose regimen platform 156 can access product or drug manufacturer labeling information for the prescribed drug. Based on information obtained from the labeling information (or dosing data), the alternate dose regimen platform 156 can generate a plurality of different (alternate) dose regimens that achieve the same or substantially the same level of efficacy as the prescribed dose. The alternate dose regimen platform 156 can generate a first plurality of indicators 422 representing a first set of alternate medication regimens having a first level of accuracy. The alternate dose regimen platform 156 can generate a first plurality of indicators 424 representing a second set of alternate medication regimens having a second level of accuracy. Each of the plurality of indicators 424 and 422 can be associated with a different combination of drug vials and/or different combination of intervals for delivery of the dose to achieve the same level of efficacy as the prescribed dose.

In some examples, the alternate dose regimen platform 156 can highlight or visually distinguish particular ones of the plurality of indicators 424 and 422 that are recommended by the model (e.g., the neural network). The recommended plurality of indicators 424 and 422 can correspond to alternate dose regimens that correspond to one or more criteria (discussed above), such as are associated with a particular inventory level, are associated with a particular level of adherence, are associated with a particular or acceptable level of side effects, are suitable for a particular age group, and so forth. In some examples, the alternate dose regimen platform 156 also generates a visual indicator 426 that highlights one or more of the plurality of indicators 424 and 422 which include a particular type of drug vial in the combination of vials represented by the respective plurality of indicators 424 and 422. For example, if a given one of the plurality of indicators 424 and 422 includes a 30 mg drug vial in the combination used to achieve a particular dose regimen, the visual indicator 426 can be used to highlight that particular given one of the plurality of indicators 424 and 422. For example, if a given one of the plurality of indicators 424 and 422 includes more than one injection in the combination of drug vials used to achieve a particular dose regimen, the visual indicator 426 can be used to highlight that particular given one of the plurality of indicators 424 and 422. In some cases, the particular type of drug vial that is highlighted can correspond to a drug vial with a particular criterion (e.g., having a certain level of side effects, efficacy, or which cannot be combined in a single syringe with other drug vials, or dose regimens which include two or more injections in the combination of drug vials). The visual indicators 422, 424, 426 can indicate a range, that is have at least two dimensions and may each include a display that is distinct from the other indicators that are shown on a graphical user interface. The visual indicators can show a dose range (inclusive of total dose, frequency of dose, patient weight, or combinations thereof). The visual indicators for a dose range can also account for injection count. Additional data can be used in the calculation, for example, vial count, national drug code (NDC) count. The visual elements displayed can also include a graphical representation of the prescribed dose and the waste associated with eh prescribed dose.

The alternate dose regimen platform 156 can receive input from a user (e.g., a pharmacist or physician) that selects a given one of the plurality of indicators 424 and 422. For example, as shown in FIG. 5, the alternate dose regimen platform 156 can receive input that selects the indicator 510. In response, the alternate dose regimen platform 156 can update the vial combination window 430 to represent the dose regimen associated with the indicator 510 that was selected. Namely, the alternate dose regimen platform 156 can present an updated vial combination window 520. The updated vial combination window 520 represents a new vial combination that achieves the same level of efficacy or provides the prescribed dose to the patient. For example, the updated vial combination window 520 specifies that the new dose included in the updated vial combination is associated with 1 mg of drug waste or no drug waste at all. Namely, the vial combination window 520 can specify three vials including a 30 mg vial, a 60 mg vial, and a 105 mg vial which total to 195 mg of dose. The vial combination window 520 can display a visual indicator 524 that highlights those dose vials (e.g., the 60 mg vial and the 105 mg vial) that can be combined into a single injection or syringe. The total 195 mg of the dose is only 1 mg greater than the prescribed dose of 194 which substantially reduces drug waste from the prescribed drug vials of 210 mg of dose. Based on the information contained in the vial combination window 520, the user can send a notification to a prescribing physician or doctor to update the prescription and/or can dispense the medication according to the dose regiment specified in the vial combination window 520.

In some examples, the alternate dose regimen platform 156 can continue receiving additional user inputs (or detect that a cursor highlights different ones of the plurality of indicators 424 and 422. As each of the of the plurality of indicators 424 and 422 is highlighted or selected, the alternate dose regimen platform 156 updates the information presented in the vial combination window 520 to represent the alternate dose regimen associated with the highlighted or selected one of the plurality of indicators 424 and 422. In this way, a user can see differences in drug combination vials associated with different alternate prescription regimens using different doses and/or different dose delivery intervals.

Figure 6:
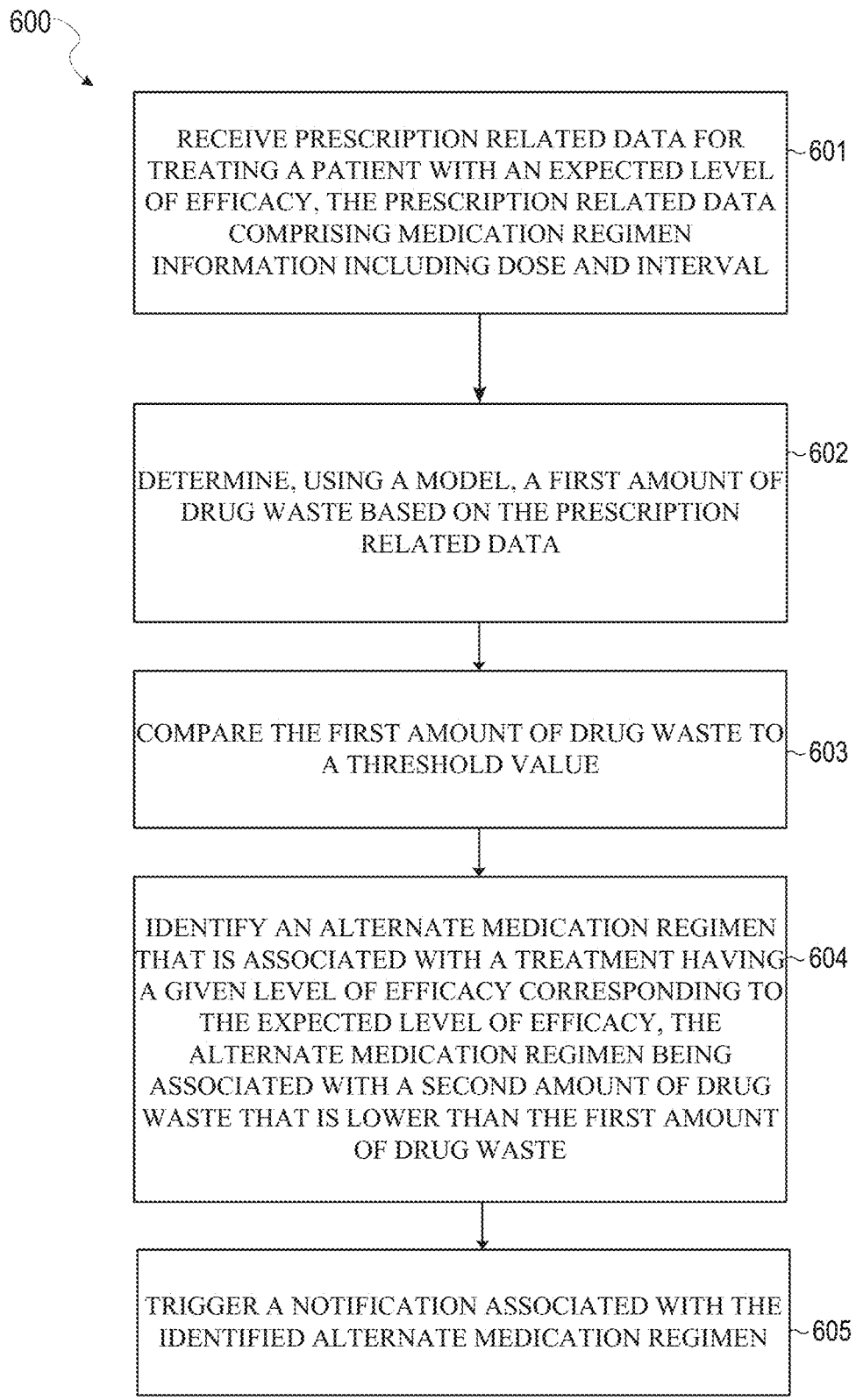
FIG. 6 is a flowchart illustrating example operations of the alternate dose regimen platform, according to example embodiments.

FIG. 6 is a flowchart illustrating example operations of the dose regimen computation system in performing process 600, according to example embodiments. The process 600 may be embodied in computer-readable instructions for execution by one or more processors such that the operations of the process 600 may be performed in part or in whole by the functional components of the system 100; accordingly, the process 600 is described below by way of example with reference thereto. However, in other embodiments, at least some of the operations of the process 600 may be deployed on various other hardware configurations. Some or all of the operations of process 600 can be in parallel, out of order, or entirely omitted.

At operation 601, the system 100 receives prescription related data for treating a patient with an expected level of efficacy, the prescription related data comprising medication regimen information including dose and interval, as discussed herein. The prescription related data can include (additionally or in place of other data) patient information, e.g., the weight of the patient. The prescription related data can include a vial count for the prescription. The prescription related data can include an injection count for the prescribed drug dose regimen. The prescription related data can include an NDC count for the drug that is in the prescription. Other prescription related data that can be used includes pharmacy data, e.g., inventory expiration data, patient adherence data, patient demographics, dispensing volume, and the like. Prescription related data can also include physician data, e.g., historical prescribing preferences for a particular drug.

At operation 602, the system 100 determines, using a model, a first amount of drug waste based on the prescription related data, as discussed above.

At operation 603, the system 100 compares the first amount of drug waste to a threshold value, as discussed above.

At operation 604, the system 100 identifies an alternate medication regimen that is associated with a treatment having a given level of efficacy corresponding to the expected level of efficacy, the alternate medication regimen being associated with a second amount of drug waste that is lower than the first amount of drug waste, as discussed above.

At operation 605, the system 100 triggers a notification associated with the identified alternate medication regimen, as discussed above.

Figure 7:
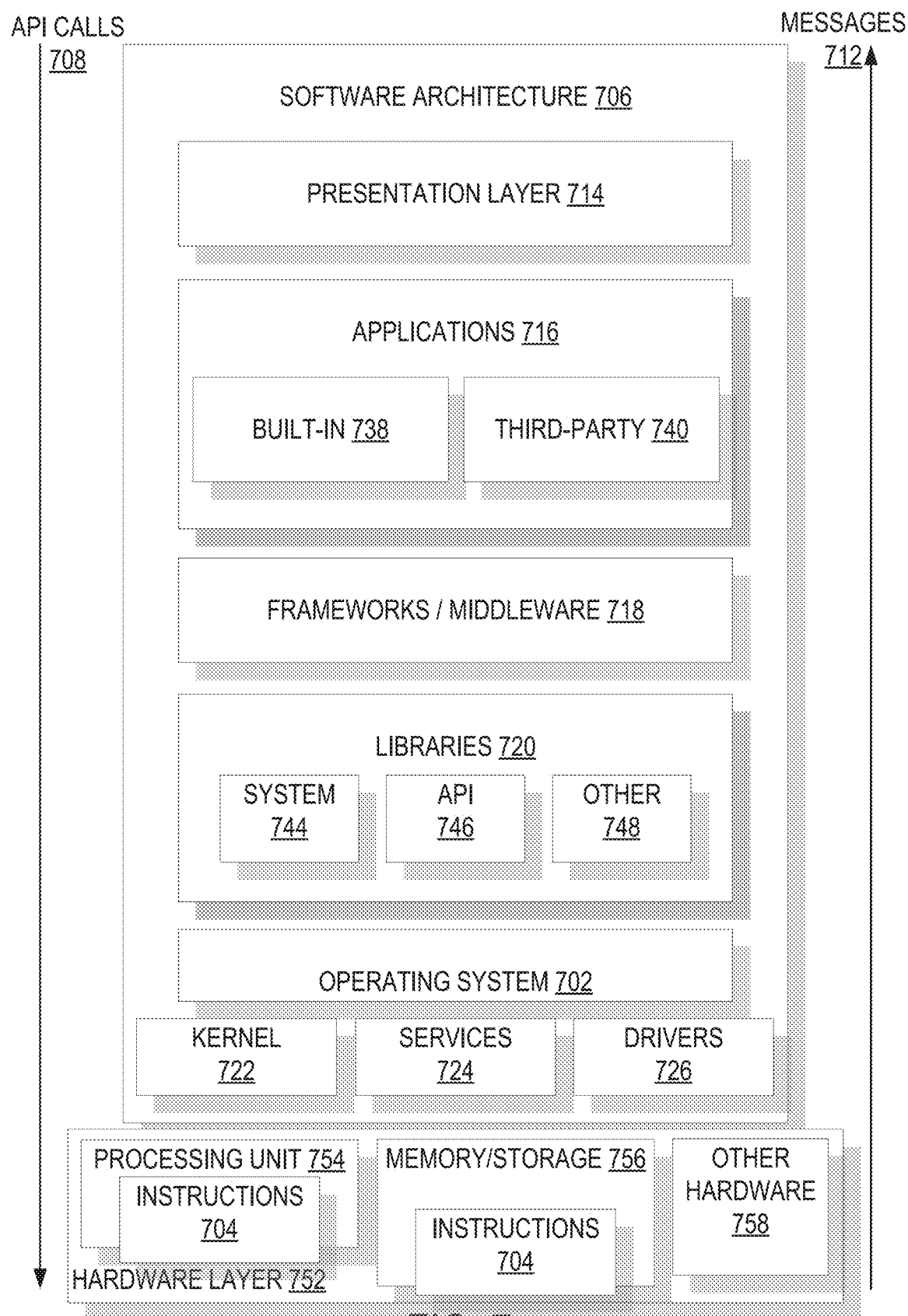
FIG. 7 is a block diagram illustrating an example software architecture, which may be used in conjunction with various hardware architectures herein described.

FIG. 7 is a block diagram illustrating an example software architecture 706, which may be used in conjunction with various hardware architectures herein described. FIG. 7 is a non-limiting example of a software architecture and it will be appreciated that many other architectures may be implemented to facilitate the functionality described herein. The software architecture 706 may execute on hardware such as machine 800 of FIG. 8 that includes, among other things, processors 804, memory 814, and input/output (I/O) components 818. A representative hardware layer 752 is illustrated and can represent, for example, the machine 800 of FIG. 8. The representative hardware layer 752 includes a processing unit 754 having associated executable instructions 704. Executable instructions 704 represent the executable instructions of the software architecture 706, including implementation of the methods, components, and so forth described herein. The hardware layer 752 also includes memory and/or storage devices memory/storage 756, which also have executable instructions 704. The hardware layer 752 may also comprise other hardware 758. The software architecture 706 may be deployed in any one or more of the components shown in FIG. 1. The software architecture 706 can be utilized to apply a machine learning technique or model to generate a prediction of a plurality of scores for each of the plurality of medications for a patient each being indicative of a likelihood that the patient will be converted from the current dispensing method to an alternate dispensing method.

In the example architecture of FIG. 7, the software architecture 706 may be conceptualized as a stack of layers where each layer provides particular functionality. For example, the software architecture 706 may include layers such as an operating system 702, libraries 720, frameworks/middleware 718, applications 716, and a presentation layer 714. Operationally, the applications 716 and/or other components within the layers may invoke API calls 708 through the software stack and receive messages 712 in response to the API calls 708. The layers illustrated are representative in nature and not all software architectures have all layers. For example, some mobile or special purpose operating systems may not provide a frameworks/middleware 718, while others may provide such a layer. Other software architectures may include additional or different layers.

The operating system 702 may manage hardware resources and provide common services. The operating system 702 may include, for example, a kernel 722, services 724, and drivers 726. The kernel 722 may act as an abstraction layer between the hardware and the other software layers. For example, the kernel 722 may be responsible for memory management, processor management (e.g., scheduling), component management, networking, security settings, and so on. The services 724 may provide other common services for the other software layers. The drivers 726 are responsible for controlling or interfacing with the underlying hardware. For instance, the drivers 726 include display drivers, camera drivers, Bluetooth® drivers, flash memory drivers, serial communication drivers (e.g., Universal Serial Bus (USB) drivers), Wi-Fi® drivers, audio drivers, power management drivers, and so forth depending on the hardware configuration.

The libraries 720 provide a common infrastructure that is used by the applications 716 and/or other components and/or layers. The libraries 720 provide functionality that allows other software components to perform tasks in an easier fashion than to interface directly with the underlying operating system 702 functionality (e.g., kernel 722, services 724 and/or drivers 726). The libraries 720 may include system libraries 744 (e.g., C standard library) that may provide functions such as memory allocation functions, string manipulation functions, mathematical functions, and the like. In addition, the libraries 720 may include API libraries 746 such as media libraries (e.g., libraries to support presentation and manipulation of various media format such as MPREG4, H.264, MP3, AAC, AMR, JPG, PNG), graphics libraries (e.g., an OpenGL framework that may be used to render two-dimensional and three-dimensional in a graphic content on a display), database libraries (e.g., SQLite that may provide various relational database functions), web libraries (e.g., WebKit that may provide web browsing functionality), and the like. The libraries 720 may also include a wide variety of other libraries 748 to provide many other APIs to the applications 716 and other software components/devices.

The frameworks/middleware 718 (also sometimes referred to as middleware) provide a higher-level common infrastructure that may be used by the applications 716 and/or other software components/devices. For example, the frameworks/middleware 718 may provide various graphic user interface functions, high-level resource management, high-level location services, and so forth. The frameworks/middleware 718 may provide a broad spectrum of other APIs that may be utilized by the applications 716 and/or other software components/devices, some of which may be specific to a particular operating system 702 or platform.

The applications 716 include built-in applications 738 and/or third-party applications 740. Examples of representative built-in applications 738 may include, but are not limited to, a contacts application, a browser application, a book reader application, a location application, a media application, a messaging application, and/or a game application. Third-party applications 740 may include an application developed using the ANDROID™ or IOS™ software development kit (SDK) by an entity other than the vendor of the particular platform, and may be mobile software running on a mobile operating system such as IOS™, ANDROID™, WINDOWS® Phone, or other mobile operating systems. The third-party applications 740 may invoke the API calls 708 provided by the mobile operating system (such as operating system 702) to facilitate functionality described herein.

The applications 716 may use built-in operating system functions (e.g., kernel 722, services 724, and/or drivers 726), libraries 720, and frameworks/middleware 718 to create UIs to interact with users of the system. Alternatively, or additionally, in some systems, interactions with a user may occur through a presentation layer, such as presentation layer 714. In these systems, the application/component "logic" can be separated from the aspects of the application/component that interact with a user.

Figure 8:
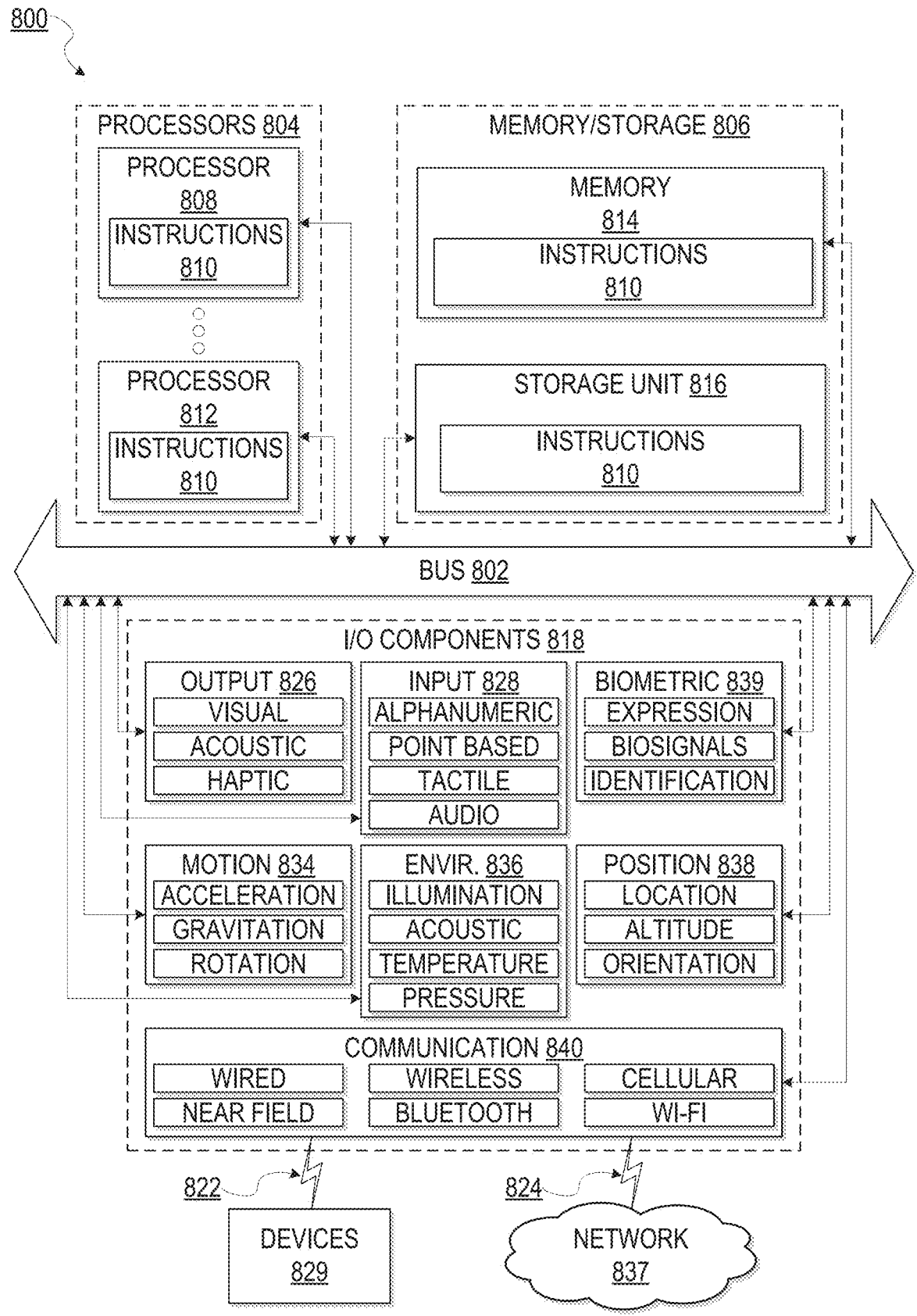
FIG. 8 is a block diagram illustrating components of a machine, according to some example embodiments.

FIG. 8 is a block diagram illustrating components of a machine 800, according to some example embodiments, able to read instructions from a machine-readable medium (e.g., a machine-readable storage medium) and perform any one or more of the methodologies discussed herein. Specifically, FIG. 8 shows a diagrammatic representation of the machine 800 in the example form of a computer system, within which instructions 810 (e.g., software, a program, an application, an applet, an app, or other executable code) for causing the machine 800 to perform any one or more of the methodologies discussed herein may be executed. For example, the instructions 810 may be executed by the system 100 to process a combination of patient-drug features with a trained machine learning model to predict a plurality of scores for each of the plurality of medications each being indicative of a likelihood that the patient will be converted from the current dispensing method to an alternate dispensing method.

As such, the instructions 810 may be used to implement devices or components described herein. The instructions 810 transform the general, non-programmed machine 800 into a particular machine 800 programmed to carry out the described and illustrated functions in the manner described. For example, the machine 800 may, in alternative embodiments, operate as a standalone device or may be coupled (e.g., networked) to other machines. In a networked deployment, the machine 800 may operate in the capacity of a server machine or a client machine in a server-client network environment, or as a peer machine in a peer-to-peer (or distributed) network environment. The machine 800 may comprise, but not be limited to a server computer, a client computer, a personal computer (PC), a tablet computer, a laptop computer, a netbook, a STB, a PDA, an entertainment media system, a cellular telephone, a smart phone, a mobile device, a wearable device (e.g., a smart watch), a smart home device (e.g., a smart appliance), other smart devices, a web appliance, a network router, a network switch, a network bridge, or any machine capable of executing the instructions 810, sequentially or otherwise, that specify actions to be taken by machine 800. Further, while only a single machine 800 is illustrated, the term "machine" shall also be taken to include a collection of machines that individually or jointly execute the instructions 810 to perform any one or more of the methodologies discussed herein.

The machine 800 may include processors 804, memory/storage 806, and I/O components 818, which may be configured to communicate with each other such as via a bus 802. In an example embodiment, the processors 804 (e.g., a central processing unit (CPU), a reduced instruction set computing (RISC) processor, a complex instruction set computing (CISC) processor, a graphics processing unit (GPU), a digital signal processor (DSP), an application-specific integrated circuit (ASIC), a radio-frequency integrated circuit (RFIC), another processor, or any suitable combination thereof) may include, for example, a processor 808 and a processor 812 that may execute the instructions 810. The term "processor" is intended to include multi-core processors 804 that may comprise two or more independent processors (sometimes referred to as "cores") that may execute instructions contemporaneously. Although FIG. 8 shows multiple processors 804, the machine 800 may include a single processor with a single core, a single processor with multiple cores (e.g., a multi-core processor), multiple processors with a single core, multiple processors with multiple cores, or any combination thereof. For example the machine 800 may operate, e.g., using its processors 804 and instructions stored in memory/storage 806, to: receive prescription related data for treating a patient with an expected level of efficacy, the prescription related data comprising medication regimen information including dose and interval; determine, using a model, a first amount of drug waste based on the prescription related data, comparing the first amount of drug waste to a threshold value; and in response to determining that the first amount of drug waste transgresses the threshold value, identify an alternate medication regimen that is associated with a treatment having a given level of efficacy corresponding to the expected level of efficacy, the alternate medication regimen being associated with a second amount of drug waste that is lower than the first amount of drug waste. The machine 800 may further operate to trigger a notification associated with the alternate medication regimen.

The memory/storage 806 may include a memory 814, such as a main memory, or other memory storage, database 152, and a storage unit 816, both accessible to the processors 804 such as via the bus 802. The storage unit 816 and memory 814 store the instructions 810 embodying any one or more of the methodologies or functions described herein. The instructions 810 may also reside, completely or partially, within the memory 814, within the storage unit 816, within at least one of the processors 804 (e.g., within the processor's cache memory), or any suitable combination thereof, during execution thereof by the machine 800. Accordingly, the memory 814, the storage unit 816, and the memory of processors 804 are examples of machine-readable media. In an example, the memory/storage 816 is a machine-readable medium that can store prescription data and data relating to different dosing schedules that meet an acceptable therapeutic level for a particular drug as described herein. In an example, the memory/storage 816 stores at least a first indicator for the GUI to show the prescribed drug dose, a second indicator to show a therapeutically acceptable alternate drug dose, and a third indicator to show an alternate drug dose that is not therapeutically acceptable.

The I/O components 818 may include a wide variety of components to receive input, provide output, produce output, transmit information, exchange information, capture measurements, and so on. The specific I/O components 818 that are included in a particular machine 800 will depend on the type of machine. For example, portable machines such as mobile phones will likely include a touch input device or other such input mechanisms, while a headless server machine will likely not include such a touch input device. It will be appreciated that the I/O components 818 may include many other components that are not shown in FIG. 8. The I/O components 818 are grouped according to functionality merely for simplifying the following discussion and the grouping is in no way limiting. In various example embodiments, the I/O components 818 may include output components 826 and input components 828. The output components 826 may include visual components (e.g., a display such as a plasma display panel (PDP), a light emitting diode (LED) display, a liquid crystal display (LCD), a projector, or a cathode ray tube (CRT)), acoustic components (e.g., speakers), haptic components (e.g., a vibratory motor, resistance mechanisms), other signal generators, and so forth. The input components 828 may include alphanumeric input components (e.g., a keyboard, a touch screen configured to receive alphanumeric input, a photo-optical keyboard, or other alphanumeric input components), point-based input components (e.g., a mouse, a touchpad, a trackball, a joystick, a motion sensor, or other pointing instrument), tactile input components (e.g., a physical button, a touch screen that provides location and/or force of touches or touch gestures, or other tactile input components), audio input components (e.g., a microphone), and the like.

In further example embodiments, the I/O components 818 may include biometric components 839, motion components 834, environmental components 836, or position components 838 among a wide array of other components. For example, the biometric components 839 may include components to detect expressions (e.g., hand expressions, facial expressions, vocal expressions, body gestures, or eye tracking), measure biosignals (e.g., blood pressure, heart rate, body temperature, perspiration, or brain waves), identify a person (e.g., voice identification, retinal identification, facial identification, fingerprint identification, or electroencephalogram based identification), and the like. The motion components 834 may include acceleration sensor components (e.g., accelerometer), gravitation sensor components, rotation sensor components (e.g., gyroscope), and so forth. The environmental components 836 may include, for example, illumination sensor components (e.g., photometer), temperature sensor components (e.g., one or more thermometer that detect ambient temperature), humidity sensor components, pressure sensor components (e.g., barometer), acoustic sensor components (e.g., one or more microphones that detect background noise), proximity sensor components (e.g., infrared sensors that detect nearby objects), gas sensors (e.g., gas detection sensors to detection concentrations of hazardous gases for safety or to measure pollutants in the atmosphere), or other components that may provide indications, measurements, or signals corresponding to a surrounding physical environment. The position components 838 may include location sensor components (e.g., a GPS receiver component), altitude sensor components (e.g., altimeters or barometers that detect air pressure from which altitude may be derived), orientation sensor components (e.g., magnetometers), and the like.

Communication may be implemented using a wide variety of technologies. The I/O components 818 may include communication components 840 operable to couple the machine 800 to a network 837 or devices 829 via coupling 824 and coupling 822, respectively. For example, the communication components 840 may include a network interface component or other suitable device to interface with the network 837. In further examples, communication components 840 may include wired communication components, wireless communication components, cellular communication components, Near Field Communication (NFC) components, Bluetooth® components (e.g., Bluetooth® Low Energy), Wi-Fi® components, and other communication components to provide communication via other modalities. The devices 829 may be another machine or any of a wide variety of peripheral devices (e.g., a peripheral device coupled via a USB). The communication system 840 may produce a carrier signal in which is imbedded data representing the range of different prescriptions that meet a level of therapeutic effect while reducing wither the waste of the number of vials needed to fulfill a treatment regimen for a patient. In an example embodiment, the communication system 840 may produce a carrier signal in which is imbedded data representing the requested change in the prescription to reduce waste as described herein. In an example embodiment, the communication system 840 may produce a carrier signal in which is imbedded data representing the graphical user interface as described herein. The communication components 840 can transmit a trigger notification to suggest an alternate dosing regimen for a prescribed drug.

Moreover, the communication components 840 may detect identifiers or include components operable to detect identifiers. For example, the communication components 840 may include Radio Frequency Identification (RFID) tag reader components, NFC smart tag detection components, optical reader components (e.g., an optical sensor to detect one-dimensional bar codes such as Universal Product Code (UPC) bar code, multi-dimensional bar codes such as Quick Response (QR) code, Aztec code, Data Matrix, Dataglyph, MaxiCode, PDF417, Ultra Code, UCC RSS-2D bar code, and other optical codes), or acoustic detection components (e.g., microphones to identify tagged audio signals). In addition, a variety of information may be derived via the communication components 840, such as location via Internet Protocol (IP) geo-location, location via Wi-Fi® signal triangulation, location via detecting a NFC beacon signal that may indicate a particular location, and so forth.

Figure 9:
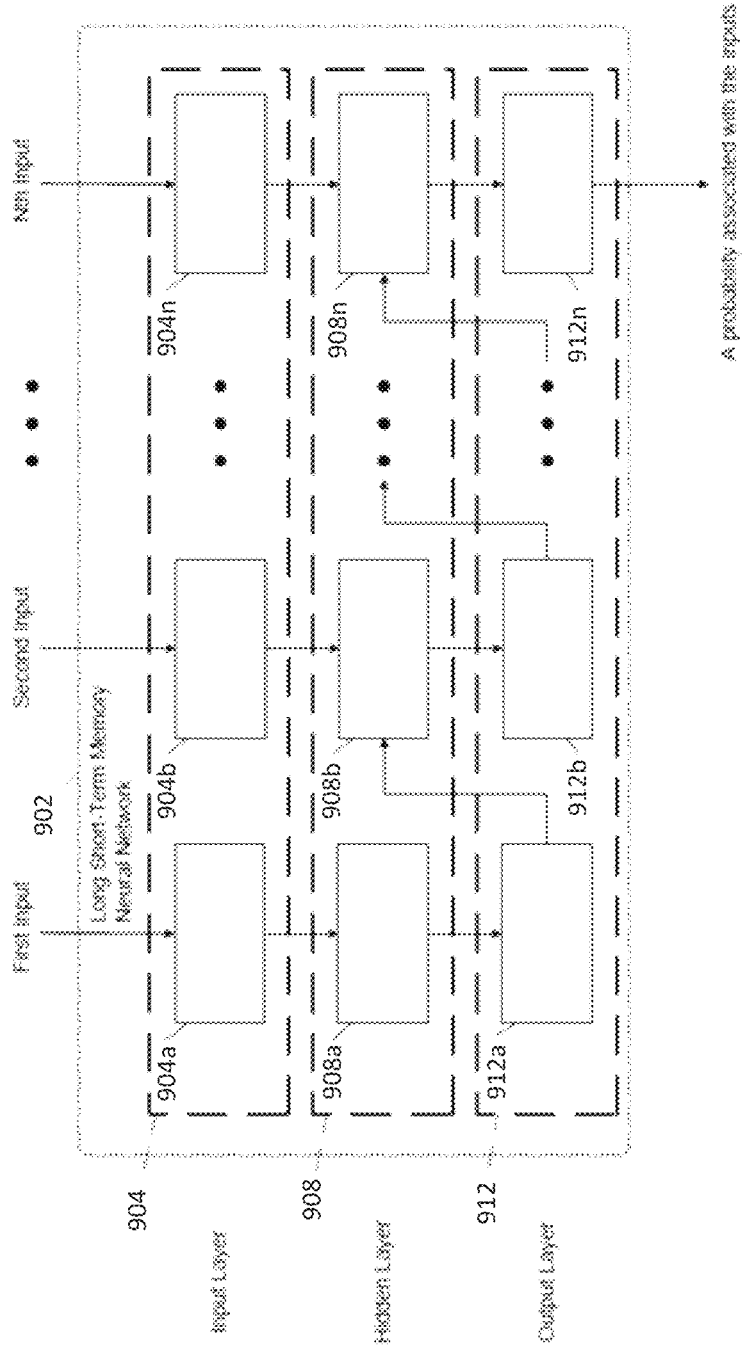
FIG. 9 is a functional block diagram of an example neural network that can be used for the inference engine or other functions (e.g., engines) as described herein to produce a predictive model.

FIG. 9 is a functional block diagram of an example neural network 902 that can be used for the inference engine or other functions (e.g., engines) as described herein to produce a predictive model. The predictive model can identify alternate medication regimen(s) given prescription related data for a particular medication regimen. In an example, the neural network 902 can be a LSTM neural network. In an example, the neural network 902 can be a recurrent neural networks (RNN). The example neural network 902 may be used to implement the machine learning as described herein, and various implementations may use other types of machine learning networks. The neural network 902 includes an input layer 904, a hidden layer 908, and an output layer 912. The input layer 904 includes inputs 904a, 904b . . . 904n. The hidden layer 908 includes neurons 908a, 908b . . . 908n. The output layer 912 includes outputs 912a, 912b . . . 912n.

Each neuron of the hidden layer 908 receives an input from the input layer 904 and outputs a value to the corresponding output in the output layer 912. For example, the neuron 908a receives an input from the input 904a and outputs a value to the output 912a. Each neuron, other than the neuron 908a, also receives an output of a previous neuron as an input. For example, the neuron 908b receives inputs from the input 904b and the output 912a. In this way the output of each neuron is fed forward to the next neuron in the hidden layer 908. The last output 912n in the output layer 912 outputs a probability associated with the inputs 904a-904n. Although the input layer 904, the hidden layer 908, and the output layer 912 are depicted as each including three elements, each layer may contain any number of elements. Neurons can include one or more adjustable parameters, weights, rules, criteria, or the like.

In various implementations, each layer of the neural network 902 must include the same number of elements as each of the other layers of the neural network 902. For example, training prescription related data features may be processed to create the inputs 904a-904n. The neural network 902 may implement a model to produce an alternate medication regimen for at least one of the prescription related data features. In an example embodiment, the alternate medication regimen includes a particular combination of different vials (each having a different amount of medication) and/or a particular delivery interval. More specifically, the inputs 904a-904n can include prescription related data features (binary, vectors, factors or the like) stored in the storage device 110. The prescription related data features can specify a patient weight or other information together with a particular prescription regimen including a dose and interval and/or a particular combination of vials to achieve the dose and interval. Other data features can include NDC count, total dose, frequency of injection, vial count, inventory expiration date, patient adherence, patient demographics, physician prescribing preferences, dispense volume and the like.

In an example, an input can specify a vial or set of vials that cannot be combined with each other in the same syringe. The prescription related data features can be provided to neurons 908a-908n for analysis and connections between the known facts. The neurons 908a-908n, upon finding connections, provides the potential connections as outputs to the output layer 912, which determines set of alternate medication regimens from the prescription related data features. For example, the neurons 908a-908n can receive multiple prescription related data features about a patient.

The neural network 902 can perform any of the above calculations. The output of the neural network 902 can be used to trigger a notification associated with an alternate medication regimen. For example, the notification can be provided to a PBM, health plan manager, pharmacy, physician, caregiver, and/or any combination thereof to select one or more associated patients or medication regiments for an alternate medication regimen or for particular prescription related data.

In some embodiments, a convolutional neural network may be implemented. Similar to neural networks, convolutional neural networks include an input layer, a hidden layer, and an output layer. However, in a convolutional neural network, the output layer includes one fewer output than the number of neurons in the hidden layer and each neuron is connected to each output. Additionally, each input in the input layer is connected to each neuron in the hidden layer. In other words, input 904a is connected to each of neurons 908a, 908b . . . 908n.

The present system can further provide the change in dosing regimen, e.g., when the prescription is changed to reduced waste or the number of vials to either a regulatory system, clinical investigation system, or the pharmaceutical manufacturer system. The change in the dosing regimen can be used by either one of these systems to further investigate the efficacy of the dosing regimen of the drug. In an example embodiment, the present system is separate from the efficacy investigation systems that set an effective dosing schedule for a particular drug. The prescription change can also be used by these systems to check for drug interactions.

Glossary

"CARRIER SIGNAL" in this context refers to any intangible medium that is capable of storing, encoding, or carrying transitory or non-transitory instructions for execution by the machine, and includes digital or analog communications signals or other intangible medium to facilitate communication of such instructions. Instructions may be transmitted or received over the network using a transitory or non-transitory transmission medium via a network interface device and using any one of a number of well-known transfer protocols.

"CLIENT DEVICE" in this context refers to any machine that interfaces to a communications network to obtain resources from one or more server systems or other client devices. A client device may be, but is not limited to, a mobile phone, desktop computer, laptop, PDA, smart phone, tablet, ultra-book, netbook, laptop, multi-processor system, microprocessor-based or programmable consumer electronics, game console, set-top box, or any other communication device that a user may use to access a network.

"COMMUNICATIONS NETWORK" in this context refers to one or more portions of a network that may be an ad hoc network, an intranet, an extranet, a virtual private network (VPN), a LAN, a wireless LAN (WLAN), a wide area network (WAN), a wireless WAN (WWAN), a metropolitan area network (MAN), the Internet, a portion of the Internet, a portion of the Public Switched Telephone Network (PSTN), a plain old telephone service (POTS) network, a cellular telephone network, a wireless network, a Wi-Fi® network, another type of network, or a combination of two or more such networks. For example, a network or a portion of a network may include a wireless or cellular network and the coupling may be a Code Division Multiple Access (CDMA) connection, a Global System for Mobile communications (GSM) connection, or other type of cellular or wireless coupling. In this example, the coupling may implement any of a variety of types of data transfer technology, such as Single Carrier Radio Transmission Technology (1xRTT), Evolution-Data Optimized (EVDO) technology, General Packet Radio Service (GPRS) technology, Enhanced Data rates for GSM Evolution (EDGE) technology, third Generation Partnership Project (3GPP) including 3G, fourth generation wireless (4G) networks, Universal Mobile Telecommunications System (UMTS), High Speed Packet Access (HSPA), Worldwide Interoperability for Microwave Access (WiMAX), Long Term Evolution (LTE) standard, others defined by various standard setting organizations, other long range protocols, or other data transfer technology.

"MACHINE-READABLE MEDIUM" in this context refers to a component, device, or other tangible media able to store instructions and data temporarily or permanently and may include, but is not limited to, random-access memory (RAM), read-only memory (ROM), buffer memory, flash memory, optical media, magnetic media, cache memory, other types of storage (e.g., Erasable Programmable Read-Only Memory (EEPROM)) and/or any suitable combination thereof. The term "machine-readable medium" should be taken to include a single medium or multiple media (e.g., a centralized or distributed database, or associated caches and servers) able to store instructions. The term "machine-readable medium" shall also be taken to include any medium, or combination of multiple media, that is capable of storing instructions (e.g., code) for execution by a machine, such that the instructions, when executed by one or more processors of the machine, cause the machine to perform any one or more of the methodologies described herein. Accordingly, a "machine-readable medium" refers to a single storage apparatus or device, as well as "cloud-based" storage systems or storage networks that include multiple storage apparatus or devices. The term "machine-readable medium" excludes signals per se.

"COMPONENT" in this context refers to a device, physical entity, or logic having boundaries defined by function or subroutine calls, branch points, APIs, or other technologies that provide for the partitioning or modularization of particular processing or control functions. Components may be combined via their interfaces with other components to carry out a machine process. A component may be a packaged functional hardware unit designed for use with other components and a part of a program that usually performs a particular function of related functions. Components may constitute either software components (e.g., code embodied on a machine-readable medium) or hardware components. A "hardware component" is a tangible unit capable of performing certain operations and may be configured or arranged in a certain physical manner. In various example embodiments, one or more computer systems (e.g., a standalone computer system, a client computer system, or a server computer system) or one or more hardware components of a computer system (e.g., a processor or a group of processors) may be configured by software (e.g., an application or application portion) as a hardware component that operates to perform certain operations as described herein.

A hardware component may also be implemented mechanically, electronically, or any suitable combination thereof. For example, a hardware component may include dedicated circuitry or logic that is permanently configured to perform certain operations. A hardware component may be a special-purpose processor, such as a Field-Programmable Gate Array (FPGA) or an ASIC. A hardware component may also include programmable logic or circuitry that is temporarily configured by software to perform certain operations. For example, a hardware component may include software executed by a general-purpose processor or other programmable processor. Once configured by such software, hardware components become specific machines (or specific components of a machine) uniquely tailored to perform the configured functions and are no longer general-purpose processors. It will be appreciated that the decision to implement a hardware component mechanically, in dedicated and permanently configured circuitry, or in temporarily configured circuitry (e.g., configured by software) may be driven by cost and time considerations. Accordingly, the phrase "hardware component" (or "hardware-implemented component") should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware components are temporarily configured (e.g., programmed), each of the hardware components need not be configured or instantiated at any one instance in time. For example, where a hardware component comprises a general-purpose processor configured by software to become a special-purpose processor, the general-purpose processor may be configured as respectively different special-purpose processors (e.g., comprising different hardware components) at different times. Software accordingly configures a particular processor or processors, for example, to constitute a particular hardware component at one instance of time and to constitute a different hardware component at a different instance of time.

Hardware components can provide information to, and receive information from, other hardware components. Accordingly, the described hardware components may be regarded as being communicatively coupled. Where multiple hardware components exist contemporaneously, communications may be achieved through signal transmission (e.g., over appropriate circuits and buses) between or among two or more of the hardware components. In embodiments in which multiple hardware components are configured or instantiated at different times, communications between such hardware components may be achieved, for example, through the storage and retrieval of information in memory structures to which the multiple hardware components have access. For example, one hardware component may perform an operation and store the output of that operation in a memory device to which it is communicatively coupled. A further hardware component may then, at a later time, access the memory device to retrieve and process the stored output.

Hardware components may also initiate communications with input or output devices and can operate on a resource (e.g., a collection of information). The various operations of example methods described herein may be performed, at least partially, by one or more processors that are temporarily configured (e.g., by software) or permanently configured to perform the relevant operations. Whether temporarily or permanently configured, such processors may constitute processor-implemented components that operate to perform one or more operations or functions described herein. As used herein, "processor-implemented component" refers to a hardware component implemented using one or more processors. Similarly, the methods described herein may be at least partially processor-implemented, with a particular processor or processors being an example of hardware. For example, at least some of the operations of a method may be performed by one or more processors or processor-implemented components. Moreover, the one or more processors may also operate to support performance of the relevant operations in a "cloud computing" environment or as a "software as a service" (SaaS). For example, at least some of the operations may be performed by a group of computers (as examples of machines including processors), with these operations being accessible via a network (e.g., the Internet) and via one or more appropriate interfaces (e.g., an API). The performance of certain of the operations may be distributed among the processors, not only residing within a single machine, but deployed across a number of machines. In some example embodiments, the processors or processor-implemented components may be located in a single geographic location (e.g., within a home environment, an office environment, or a server farm). In other example embodiments, the processors or processor-implemented components may be distributed across a number of geographic locations.

"PROCESSOR" in this context refers to any circuit or virtual circuit (a physical circuit emulated by logic executing on an actual processor) that manipulates data values according to control signals (e.g., "commands," "op codes," "machine code," etc.) and which produces corresponding output signals that are applied to operate a machine. A processor may, for example, be a CPU, a RISC processor, a CISC processor, a GPU, a DSP, an ASIC, a RFIC, or any combination thereof. A processor may further be a multi-core processor having two or more independent processors (sometimes referred to as "cores") that may execute instructions contemporaneously.

"TIMESTAMP" in this context refers to a sequence of characters or encoded information identifying when a certain event occurred, for example giving date and time of day, sometimes accurate to a small fraction of a second.

Changes and modifications may be made to the disclosed embodiments without departing from the scope of the present disclosure. These and other changes or modifications are intended to be included within the scope of the present disclosure, as expressed in the following claims.

The Abstract of the Disclosure is provided to comply with 37 C.F.R. § 1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter may lie in less than all features of a single disclosed embodiment. Thus, the following claims are hereby incorporated into the Detailed Description, with each claim standing on its own as a separate embodiment.

What is claimed is:

1. A method comprising:
   receiving, by one or more processors, prescription related data for treating a patient with an expected level of efficacy, the prescription related data comprising medication regimen information including dose and interval;
   determining, using a model, a first amount of drug waste based on the prescription related data;
   comparing the first amount of drug waste to a threshold value;
   in response to determining that the first amount of drug waste transgresses the threshold value,
      identifying an alternate medication regimen that is associated with a treatment having a given level of efficacy corresponding to the expected level of efficacy, the alternate medication regimen being associated with a second amount of drug waste that is lower than the first amount of drug waste; and
      triggering a notification associated with the alternate medication regimen, wherein triggering the notification comprises generating a graphical user interface comprising a plurality of interactive regions representing different medication regimens, the graphical user interface comprising:
         a prescription region representing the prescription related data and an indicator identifying the dose and interval,
         a first plurality indicators representing a first set of alternate medication regimens having a first level of accuracy, and
         a second plurality indicators representing a second set of alternate medication regimens having a second level of accuracy;
   receiving input that selects a given indicator of the first plurality of indicators or the second plurality of indicators;
   in response to receiving the input, updating the prescription region to represent a drug dose vial combination and interval associated with a given alternate medication regimen represented by the given indicator and to represent drug waste associated with the given alternate medication regimen; and
   training the model by performing operations comprising:
      obtaining a batch of training data comprising a first set of the plurality of training prescription related data features and alternate medication regimens that have been selected;
      processing the first set of the plurality of training prescription related data features by the machine learning technique to generate an estimated alternate medication regimen;
      computing a loss based on a deviation between the estimated alternate medication regimen and the corresponding alternate medication regimens of the first set of the plurality of training prescription related data features; and
      updating parameters of the machine learning technique based on the computed loss.

2. The method of claim 1, wherein the threshold value comprises 14 milligrams per dose or more.

3. The method of claim 1, wherein identifying the alternate medication regimen further comprises:
   generating a plurality of different medication regimens each being associated with the expected level of efficacy;
   computing a plurality of amounts of drug waste associated with the plurality of different medication regimens; and
   selecting the alternate medication regimen from the plurality of different medication regimens based on the plurality of amounts of drug waste.

4. The method of claim 3, further comprising:
selecting the alternate medication regimen based on a criterion and the plurality of amounts of drug waste.

5. The method of claim 4, wherein the criterion comprises a waste value that is below the threshold value.

6. The method of claim 4, wherein the criterion comprises a zero waste value.

7. The method of claim 4, wherein the criterion comprises a combination of drug dose vials that is associated with a specified level of adherence, a specified level of side effects, injection quantity, or a specified level of efficacy.

8. The method of claim 4, wherein the criterion comprises an inventory parameter of drug dose vials.

9. The method of claim 8, wherein the inventory parameter comprises a rate at which a specified type of drug dose vial is dispensed or an amount of the drug dose vial that is available.

10. The method of claim 4, wherein the dose and interval of the prescription related data is a first dose and a first interval, wherein a first of the plurality of different medication regimens comprises a second dose and the first interval, the second dose being greater than the first dose, wherein a second of the plurality of different medication regimens comprises a third dose and the first interval, the third dose being less than the first dose, wherein a fourth of the plurality of different medication regimens comprises a second dose and a second interval.

11. The method of claim 1, wherein the prescription related data is associated with a drug comprising Monoclonal antibodies with linear pharmacokinetics.

12. The method of claim 1, wherein triggering the notification comprises causing a message to be displayed by a client device associated with a pharmacy benefit manager, the message comprising the first amount of drug waste and the alternate medication regimen.

13. The method of claim 1, wherein the graphical user interface includes a third plurality of indicators that represent medication regimens of the first and second sets of alternate medication regimens having a specified type of drug dose vial.

14. The method of claim 1, wherein the model comprises a machine learning technique comprising a neural network, the machine learning technique trained to establish a relationship between a plurality of training prescription related data features and alternate medication regimens.

15. A system comprising:
one or more processors coupled to a memory comprising non-transitory computer instructions that when executed by the one or more processors perform operations comprising:
receiving prescription related data for treating a patient with an expected level of efficacy, the prescription related data comprising medication regimen information including dose and interval;
determining, using a model, a first amount of drug waste based on the prescription related data;
comparing the first amount of drug waste to a threshold value;
in response to determining that the first amount of drug waste transgresses the threshold value,
identifying an alternate medication regimen that is associated with a treatment having a given level of efficacy corresponding to the expected level of efficacy, the alternate medication regimen being associated with a second amount of drug waste that is lower than the first amount of drug waste; and
triggering a notification associated with the alternate medication regimen, wherein triggering the notification comprises generating a graphical user interface comprising a plurality of interactive regions representing different medication regimens, the graphical user interface comprising:
a prescription region representing the prescription related data and an indicator identifying the dose and interval,
a first plurality indicators representing a first set of alternate medication regimens having a first level of accuracy, and
a second plurality indicators representing a second set of alternate medication regimens having a second level of accuracy;
receiving input that selects a given indicator of the first plurality of indicators or the second plurality of indicators;
in response to receiving the input, updating the prescription region to represent a drug dose vial combination and interval associated with a given alternate medication regimen represented by the given indicator and to represent drug waste associated with the given alternate medication regimen; and
training the model by performing operations comprising:
obtaining a batch of training data comprising a first set of the plurality of training prescription related data features and alternate medication regimens that have been selected;
processing the first set of the plurality of training prescription related data features by the machine learning technique to generate an estimated alternate medication regimen;
computing a loss based on a deviation between the estimated alternate medication regimen and the corresponding alternate medication regimens of the first set of the plurality of training prescription related data features; and
updating parameters of the machine learning technique based on the computed loss.

16. The system of claim 15, wherein the threshold value comprises 14 milligrams per dose or more.

17. A non-transitory computer readable medium comprising non-transitory computer-readable instructions for performing operations comprising:
receiving prescription related data for treating a patient with an expected level of efficacy, the prescription related data comprising medication regimen information including dose and interval;
determining, using a model, a first amount of drug waste based on the prescription related data;
comparing the first amount of drug waste to a threshold value;
in response to determining that the first amount of drug waste transgresses the threshold value,
identifying an alternate medication regimen that is associated with a treatment having a given level of efficacy corresponding to the expected level of efficacy, the alternate medication regimen being associated with a second amount of drug waste that is lower than the first amount of drug waste; and
triggering a notification associated with the alternate medication regimen, wherein triggering the notification comprises generating a graphical user interface comprising a plurality of interactive regions representing different medication regimens, the graphical user interface comprising:

a prescription region representing the prescription related data and an indicator identifying the dose and interval, a first plurality indicators representing a first set of alternate medication regimens having a first level of accuracy, and a second plurality indicators representing a second set of alternate medication regimens having a second level of accuracy;

receiving input that selects a given indicator of the first plurality of indicators or the second plurality of indicators;

in response to receiving the input, updating the prescription region to represent a drug dose vial combination and interval associated with a given alternate medication regimen represented by the given indicator and to represent drug waste associated with the given alternate medication regimen; and training the model by performing operations comprising:

obtaining a batch of training data comprising a first set of the plurality of training prescription related data features and alternate medication regimens that have been selected;

processing the first set of the plurality of training prescription related data features by the machine learning technique to generate an estimated alternate medication regimen;

computing a loss based on a deviation between the estimated alternate medication regimen and the corresponding alternate medication regimens of the first set of the plurality of training prescription related data features; and updating parameters of the machine learning technique based on the computed loss.

\* \* \* \* \*